(12) United States Patent
Gjerde et al.

(10) Patent No.: US 6,372,142 B1
(45) Date of Patent: *Apr. 16, 2002

(54) COLUMN FOR DNA SEPARATION BY MATCHED ION POLYNUCLEOTIDE CHROMATOGRAPHY

(75) Inventors: Douglas T. Gjerde, Saratoga; Robert M. Haefele, Campbell; Karl H. Hecker, Milpitas; Raquel R. Roque, Campbell, all of CA (US)

(73) Assignee: Transgenomic, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,775

(22) Filed: Feb. 10, 2000

Related U.S. Application Data

(63) Continuation-in-part of application No. 09/183,123, filed on Oct. 30, 1998, now Pat. No. 6,066,258, which is a continuation-in-part of application No. 09/058,580, filed on Apr. 10, 1998, now abandoned, which is a continuation-in-part of application No. 08/748,376, filed on Nov. 13, 1996, now Pat. No. 5,772,889

(60) Provisional application No. 60/177,117, filed on Jan. 20, 2000, provisional application No. 60/167,515, filed on Nov. 24, 1999, provisional application No. 60/158,743, filed on Oct. 12, 1999, and provisional application No. 60/154,614, filed on Sep. 17, 1999.

(51) Int. Cl.[7] .............................................. B01D 15/08
(52) U.S. Cl. .................... 210/635; 210/656; 210/198.2; 435/6; 536/25.4
(58) Field of Search ................................. 210/635, 656, 210/659, 198.2; 435/6; 536/23.1, 25.4

(56) References Cited

U.S. PATENT DOCUMENTS

| 4,563,510 A | 1/1986 | Ugelstad ........................ 526/66 |
|---|---|---|
| 4,683,202 A | 7/1987 | Mullis ........................... 435/91 |
| 4,906,378 A | 3/1990 | Hagen et al. .................. 210/635 |
| 5,098,539 A | 3/1992 | Shieh ........................ 204/182.8 |
| 5,100,547 A | 3/1992 | Hardiman et al. .......... 210/198.2 |
| 5,205,929 A | 4/1993 | Carr et al. .................. 210/198.2 |
| 5,207,914 A | 5/1993 | Lin ............................. 210/635 |
| 5,316,680 A | 5/1994 | Frechet et al. ............... 210/635 |
| 5,334,310 A | 8/1994 | Frechet et al. ............ 210/198.2 |

(List continued on next page.)

FOREIGN PATENT DOCUMENTS

| EP | 0 507 591 A2 | 10/1992 | ............... 210/198.2 |
|---|---|---|---|
| WO | 94/11305 | 5/1994 | ............... 210/198.2 |
| WO | 98/40395 | 9/1998 | ............... 210/198.2 |
| WO | WO 99/39195 | 8/1999 | ............... 210/198.2 |
| WO | 00/56925 | 9/2000 | ............... 210/198.2 |

OTHER PUBLICATIONS

All–Chrom Newsletter Metal Components, A Potential Source of Interference in HPLC Analysis, Alltech–Applied Science, 25:1–6 (1986).

(List continued on next page.)

Primary Examiner—Ernest G. Therkorn
(74) Attorney, Agent, or Firm—William B. Walker

(57) ABSTRACT

An improved separation column and method for separating a mixture of double stranded DNA fragments by Matched Ion Polynucleotide Chromatography. The cylindrical column has an ID greater than about 5 mm and contains polymer beads. The beads have an average diameter of 1 to 100 microns and are unsubstituted polymer beads or are polymer beads substituted with a hydrocarbon moiety having from 1 to 1,000,000 carbons. The preferred beads are characterized by being substantially free from multivalent cations which are free to bind with DNA. The improved column provides enhanced separation of DNA fragments with sizes ranging from about 100 to 20,000 base pairs. The column also provides enhanced separation of heteroduplex and homoduplex DNA molecules in a mutation detection procedure in which the chromatography is performed under conditions effecting partial denaturation of DNA at a site of mismatched base pairs.

10 Claims, 12 Drawing Sheets

U.S. PATENT DOCUMENTS

| | | | | |
|---|---|---|---|---|
| 5,338,448 | A | | 8/1994 | Gjerde ..................... 210/198.2 |
| 5,453,185 | A | | 9/1995 | Frechet et al. ........... 210/198.2 |
| 5,522,994 | A | | 6/1996 | Frechet et al. .............. 210/635 |
| 5,585,236 | A | | 12/1996 | Bonn et al. ..................... 435/5 |
| 5,616,701 | A | | 4/1997 | Woodard et al. ........... 536/25.4 |
| 5,772,889 | A | | 6/1998 | Gjerde et al. ............... 210/635 |
| 5,795,976 | A | | 8/1998 | Oefner et al. .............. 536/25.4 |
| 5,968,361 | A | | 10/1999 | Goetzinger et al. ......... 210/635 |
| 6,024,878 | A | * | 2/2000 | Gjerde ........................ 210/635 |
| 6,066,258 | A | | 5/2000 | Gjerde et al. ............... 210/635 |
| 6,210,885 | B1 | * | 4/2001 | Gjerde ........................... 435/6 |
| 6,265,168 | B1 | * | 7/2001 | Gjerde ........................... 435/6 |

OTHER PUBLICATIONS

Apffel et al. Applications of HPLC for the Analysis of Double Stranded DNA Use of Wide Pore Silica Based Materials, ISPPP '97 17th International Symposium on the Separation of Proteins, Peptides & Polynucleotides, 26–29, (1997).

Ariyoshi et al, Crystal Structure of the Holliday Junction DNA in Complex with a Single RuvA Tetramer, Proc. Nat. Acad. Sci., 97:8257–8262, (2000).

Barder et al. Fast Chromatography and Nonporous Silica, LC–GC, 15: 918–926, (1997).

Berti, Dissertation, Untersuchungen Zur Ionenpaar–Umkehrphasen–Chromatographie Von DNA, 52–53, 1996.

Bischoff et al, Isolation of Specific Trnas Using an Ionic–Hydrophobic Mixed–Mode Chromatographic Matrix, Analytical Biochemistry, 151: 526–533 (1985).

Cabrera et al. Silica Rod—A New Challenge in Fast High-Performance Liquid Chromatography Separations, Trends in Analytical Chemistry, 17:50–53, (1998).

Chen et al. High–Speed High–Performance Liquid Chromatography of Peptides and Proteins, J. of Chromatography A, 705: 3–20, (1995).

DHPLC Workshop, Stanford University, CA, pp. 32–43 (Mar. 17, 1997).

Doris et al., Quantitative Analysis of Gene Expression by Ion–Pair High–Performance Liquid Chromatography, Journal of Chromatography, 806: 47–60, (1998).

Engelhardt et al. Polymer Encapsulated Stationary Phases: Advantages, Properties and Selectivities, Chromatographia, 27: 535–543, (1989).

Erikkson et al, Separation of DNA Restriction Fragments by Ion–Pair Chromatography, Journal of Chromatography, 359: 265–274 (1986).

Fritz et al, Quantitative Analytical Chemistry, Third Edition, pp. 378–379, Allyn & Bacon Inc. (1977).

Goodwin et al., Studies on the Preparation and Characterisation of Monodisperse Polystyrene Latices, Colloid & Polymer Sci. 252: 464–471, (1974).

Green et al. HPLC Purification of Synthetic Oligodeoxyribonucleotides Contatining Base– and Backbone–Modified Sequences, BioTechniques 19:836–841 (1993).

Green et al. Preparative Purification F Sypercoiled Plasmid DNA for the Therapeutic Applications, BioPharm, 10:52–62, (1997).

Hancock et al, High Performance Liquid Chromatography in Biotechnology,Applied Biosystems, 301–397 (1990).

Hayward–Lester et al, Rapid Quantification of Gene Expression by Competitive RT–PCR and Ion–Pair Reversed–Phase HPLC, BioTechniques, 20: 250–257 (1996).

Hayward–Lester et al., Quantification of Specific Nucleic Acids, Regulated RNA Processing and Genomic Polymorphisms Using Reversed–Phase HPLC.

He et al. Fabrication of Nanocolumns for Liquid Chromatography, Anal. Chem. 70:3790–3797, (1998).

Heftman, Chromatography, 5th Edition, Journal of Chromatography Library—51A:A299–A300, (1992).

Herold et al. Recovery of Biologicaly Active Enzymes After HPLC Separation, BioChromatography, BioTechniques, 10:656–662, (1991).

Hewlett–Packard, ZORBAX Stable Bond ZORBAX Eclipse Reverse Phase HPLC Columns, Product Specification.

Hirabayashi et al. Size–Dependent Chromatographic Separation of Double–Stranded DNA Which is not Based on Gel Permeation Mode, Analytical Biochemsitry, 178, 336–341, (1989).

Hirabayashi, Slalom Chromatography: Size–Dependent Separation of DNA Molecules by a Hydrodynamic Phenomenon, Biochemistry, 29: 9515–9521, (1990).

http://www.transgenomic.com/html/tmha.html (May 12, 1998).

Huang et al.Large–Scale Purification of Synthetic Oligonucleotides and Carcinogen–Modified Oligodeoxynucleotides on a Reverse–Phase Polystyrene (PRP–1) Column, Analytical Biochemistry, 190:21–25, (1990).

Huber et al, High–Resolution Liquid Chromatography of Oligonucleotides on Nonporous Alkylated Styrene–Divinylbenzene Copolymers, Analytical Biochemistry, 212: 351–358 (1993).

Huber et al, High–Repsolution Liquid Chromatography of DNA Fragments on Non–Porous Polystyrene–Divinylbenzene) Particles, Nucleic Acid Research, 21:1061–1066 (1993).

Huber et al, Rapid Analysis of Biopolymers on Modified Non–Porous Polystyrene–Divinylbenzene Particles, Chromatograhia, 37: 653–658 (1993).

Huber et al, Rapid and Accurate Sizing of DNA Fragments by Ion–Pair Chromatography on Alkylated Nonporous Poly-(Styrene–Divinylbenzene) Particles, Analytical Chemistry, 67: 578–585 (1995).

Huber et al., Micropellicular Stationary Phases for HighPerformance Liquid Chromatography of Double–Stranded DNA, J. of Chromatography A, 806:3–30 (1998).

Iler et al. The Chemistry of Silica (1979) John Wiley & Sons, New York.

Issaq et al. Enthalpy and Entropy Effects for Homologous Solutes in HPLC with Alkyl Chain Bonded Phases, J. of Liquid Chromatography 12: 2067–2082, (1989).

Jinno et al. Planarity Recognition of Large Polycyclic Aromatic Hydrocarbons by Various Octadecylsilica Stationary Phases in Non–Aqueous RPLC, Chromatographia, 27:285–291, (1989).

Kato et al. Separation of DNA Restriction Fragments by High–Performance Ion–Exchange Chromatography on a Non–Porous Ion Exchanger, Journal of Chromatography, 478:264–268, (1989).

Kleymenova et al, Application of High Performance Liquid Chromatography–Based Analysis of DNA Fragments to Molecular Carcinogenesis, Molecular Carcinogenesis 29:51–58 (2000).

Kwiatkowski et al. Use of RP Ion Pair Chromatography to Fractionate and Purify DNA Fragments and Monomeric Components of RNA, Acta Chemica scandinavica B. 38: 721–733, (1984).

Liu et al, Denaturing High Performance Liquid Chromatography (DHPLC) Used in the Detection of Germline and Somatic Mutations, Nucleic Acid Research, 26:1396–1400 (1998).

Maa et al, Rapid High–Performance Liquid Chromatography of Ncleic Acids with Polystyrene–Based Micropellicular Anion Exchangers, Journal of Chromatography, 508:61–73, (1990).

Melander et al., Mobile Phase Effects in Reversed–Phase Chromatography, J. of Chromatography 185: 99–109, (1979).

Mhatre et al., Interfacing Gradient Elution Ion–Exchange Chromatography (IEC) and Low Angle Laser Light Scattering Photometry (LALLS) for Analysis of Proteins, J. Chromatography, 391:139–148, (1992).

Moriyama et al. New RP HPLC Column for Oligonucleotide Separtion, Journal of Chromatography, 445:225–233, (1988).

Nahum et al. Surface Silnols in Silica–Bonded Hydrocarbonaceous Stationary Phases, J. of Chromatography, 203: 53–63, (1981).

Nakanishi et al. Double Pore Silica Gel Monolith Applied to Liquid Chromatography, J. Sol–Gel Science & Technology, 8:547–552, (1997).

Nakanishi et al., Phase Separation in Silica Sol–Gel System Containing Poly(Ethylene Oxide), Bull. Chem. Soc. Jpn., 67:1327–1335, (1994).

Oefner et al, High–Performance Liquid Chromatography for Routine Analysis of Hepatitis C Virus CDNA/PCR Products, Research Reports, 16: 898–9, 902–8 (1994).

Oefner et al, High–Resolution Liquid Chromatography of Fluorescent Dye–Labeled Nucleic Acids, Analytical Biochemistry, 223: 1–8 (1994).

Oefner et al, High–Resolution Liquid Chromatography of Nucleic Acids, American Laboratory, 26:28C–28J (1994).

Oefner et al.Poster Symposium—Session 29 Comparative DNA Sequencing by Denaturing High–Performance Liquid Chromatography (DHLPC), Am. J. Human Genet., 57:A66, (1995).

Ohmiya et al., Separation of DNA Fragments by HighResolution Ion–Exchange Chromatography on a Nonporous QA Column, Analytical Biochemistry, 189:126–130 (1990).

Petro et al, Molded Monolithic Rod of Macroprous Poly-(Styrene–Co–Divinylbenzene) as a Separation Medium for HPLC of Syntheitc Polymers, Analytical Chemistry, 68: 315–321 (1996).

Poole et al. Chromatography Today Elsevier, New York, 313–342, (1991).

Pretorius et al., A New Concept for High–Speed Liquid Chromatography, J. of Chromatography, 99:23–30, (1974).

Puresyn, Inc. Communique Physical Characteristics of the Polyflo Resin.

Saiki et al., Enzymatic Amplification of B–Globin Genomic Sequences and Restriction Site Analysis for Diagnosis of Sickle Cell Anemia, Science, 230: 1350–1354, (1985).

Schoburg et al. Immobilization of Stationary Liquids in Reversed– and Normal–Phase Liquid Chromatography, J. of Chromatography, 282: 27–39, 118 (1983).

Schoburg et al. Immobilization of Stationary Liquids of Silica Particles by Y–Radiation, Chromatographia, 18: 265–274, (1984).

Snyder et al, Introduction to Modern Liquid Chromatography, Chapter 13, pp. 173–174, 274–275, John Wiley & Sons, Inc. New York (1979).

Stober et al. Controlled Growth of Monodisperse Silica Spheres in the Micron Size Range, J. of Coll. and Interface Science 26: 62–69, (1968).

Transgenomic, Inc. Technical Note General Description: DNASep.

Ugelstad et al, Swelling of Oligomer–Polymer Particles. New Methods of Preparation of Emulsions and Polymer Dispersions, Advances in Colloid and Interface Science, 13:101–140, (1980).

Wang et al, Reversed–Phase Chromatography of Small Molecules and Peptides on a Continous Rod of Macrophorous Poly(Styrene–Codivinylbenzene), Journal of Chromatography, No. 669:230–235 (1994).

Wheals, Chemically Bonded Phases for Liquid Chromatography, J. of Chromatography (1975) 107: 402–407.

Yau et al., Modern Size–Exclusion Liquid Chromatography, John Wiley & Sons, 1979, New York pp. 343–381.

Snyder et al. Introduction to Modern Liquid Chromatography, 2nd Ed., pp. 204–205, 624, 630–632, John Wiley & Sons, Inc. New York (1979).

* cited by examiner

COLUMN FOR DNA SEPARATION BY MATCHED ION POLYNUCLEOTIDE CHROMATOGRAPHY

CROSS REFERENCE TO RELATED CO-PENDING APPLICATIONS

This application is a continuation in part of U.S. patent application Ser. No. 09/183,123 filed Oct. 30, 1998, now U.S. Pat. No. 6,066,258, which is a continuation in part of U.S. patent application Ser. No. 09/058,580 filed Apr. 10, 1998, now abandoned U.S. Pat. No. 6,066,258, which is a continuation in part of U.S. patent application Ser. No. 08/748,376 filed Nov. 13, 1996, now U.S. Pat. No. 5,772,889. This application is a regular U.S. patent application under 35 U.S.C. §111 (a) and 35 U.S.C. §1.53(b) and claims priority from the following co-pending, commonly assigned provisional applications, each filed under 35 U.S.C. §111 (b), each of which is incorporated herein by reference:

U.S. Ser. No. 60/154,614 filed Sep. 17, 1999;
U.S. Ser. No. 60/158,743 filed Oct. 12, 1999;
U.S. Ser. No. 60/167,515 filed Nov. 24, 1999;
U.S. Ser. No. 60/177,117 filed Jan. 20, 2000.

FIELD OF THE INVENTION

This invention relates to DNA separation systems and methods suitable for effecting a size-based (base pair length) separation of DNA. The invention concerns an improved separation column for increasing the range of base pair length of the DNA fragments that can be separated by Matched Ion Polynucleotide Chromatography (MIPC) and for improving the separation of heteroduplex and homoduplex DNA using MIPC under partially denaturing conditions.

BACKGROUND OF THE INVENTION

Separations of polynucleotides such as DNA have been traditionally performed using slab gel electrophoresis or capillary electrophoresis. However, liquid chromatographic separations of polynucleotides are becoming more important because of the ability to automate the analysis and to collect fractions after they have been separated. Therefore, columns for polynucleotide separation by liquid chromatography (LC) are becoming more important.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), referred to herein as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between what are called complimentary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR). Sometimes, exact replication fails and an incorrect base pairing occurs. Further replication of the new strand produces double stranded DNA offspring containing a heritable difference in the base sequence from that of the parent. Such heritable changes in base pair sequence are called mutations.

As used herein, double stranded DNA is referred to as a duplex. When a base sequence of one strand is entirely complimentary to a base sequence of the other strand, the duplex is called a homoduplex. When a duplex contains at least one base pair which is not complimentary, the duplex is called a heteroduplex. A heteroduplex is formed during DNA replication when an error is made by a DNA polymerase enzyme and a non-complimentary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has a sequence which predominates in a naturally occurring population, the sequence is generally referred to as a "wild type".

Many different types of DNA mutations are known. Examples of DNA mutations include, but are not limited to, "point mutation" or "single base pair mutations" in which an incorrect base pairing occurs. The most common point mutations comprise "transitions" in which one purine or pyrimidine base is replaced for another and "transversions" wherein a purine is substituted for a pyrimidine (and visa versa). Point mutations also comprise mutations in which a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997).

The sequence of base pairs in DNA is a code for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is therefore of great importance in diagnosing diseases, understanding the origins of disease, and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer, et al., *Proc. Natl. Acad. Sci. USA* 92:10841 (1995); Cotton, TIG 13:43 (1997)).

Alterations in a DNA sequence which are benign or have no negative consequences are sometimes called "polymorphisms". For the purposes of this application, all alterations in the DNA sequence, whether they have negative consequences or not, are defined herein as "mutations". For the sake of simplicity, the term "mutation" is used herein to mean an alteration in the base sequence of a DNA strand compared to a reference strand (generally, but not necessarily, a wild type). As used herein, the term "mutation" includes the term "polymorphism" or any other similar or equivalent term of art.

Separation of double-stranded deoxyribonucleic acids (dsDNA) fragments and detection of DNA mutations is of great importance in medicine, in the physical and social sciences, and in forensic investigations. The Human Genome Project is providing an enormous amount of genetic information and yielding new information for evaluating the links between mutations and human disorders (Guyer, et al., *Proc. Natl. Acad. Sci. USA* 92:10841 (1995)). For example, the ultimate source of disease is described by genetic code that differs from the wild type (Cotton, TIG 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* vol. 69:201 (1985)). Understanding these and other issues related to genetic coding requires the ability to identify anomalies, i.e., mutations, in a DNA fragment relative to the wild type.

Traditional chromatography is a separation process based on partitioning of mixture components between a "stationary phase" and a "mobile phase". The stationary phase is provided by the surface of solid materials which can comprise many different materials in the form of particles or passageway surfaces of cellulose, silica gel, coated silica gel, polymer beads, polysaccharides, and the like. These materials can be supported on solid surfaces such as on glass plates or packed in a column. The mobile phase can be a liquid or a gas in gas chromatography. This invention relates to liquid mobile phases.

The separation principles are generally the same regardless of the materials used, the form of the materials, or the apparatus used. The different components of a mixture have different respective degrees of solubility in the stationary phase and in the mobile phase. Therefore, as the mobile phase flows over the stationary phase, there is an equilibrium in which the sample components are partitioned between the stationary phase and the mobile phase. As the mobile phase passes through the column, the equilibrium is constantly shifted in favor of the mobile phase. This occurs because the equilibrium mixture, at any time, sees fresh mobile phase and partitions into the fresh mobile phase. As the mobile phase is carried down the column, the mobile phase sees fresh stationary phase and partitions into the stationary phase. Eventually, at the end of the column, there is no more stationary phase and the sample simply leaves the column in the mobile phase.

A separation of mixture components occurs because the mixture components have slightly different affinities for the stationary phase and/or solubilities in the mobile phase, and therefore have different partition equilibrium values. Therefore, the mixture components pass down the column at different rates.

In traditional liquid chromatography, a glass column is packed with stationary phase particles and mobile phase passes through the column, pulled only by gravity. However, when smaller stationary phase particles are used in the column, the pull of gravity alone is insufficient to cause the mobile phase to flow through the column. Instead, pressure must be applied. However, glass columns can only withstand about 200 psi. Passing a mobile phase through a column packed with 5 micron particles requires a pressure of about 2000 psi or more to be applied to the column. 5 to 10 micron particles are standard today. Particles smaller than 5 microns are used for especially difficult separations or certain special cases). This process is denoted by the term "high pressure liquid chromatography" or HPLC.

HPLC has enabled the use of a far greater variety of types of particles used to separate a greater variety of chemical structures than was possible with large particle gravity columns. The separation principle, however, is still the same.

An HPLC-based ion pairing chromatographic method was recently introduced to effectively separate mixtures of double stranded polynucleotides in general, and DNA in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. The term "Matched Ion Polynucleotide Chromatography" (MIPC) is defined herein and applied to this method because the mechanism of separation was found to be based on binding and release of the DNA from the separation surfaces rather than traditional partitioning. MIPC separates DNA fragments on the basis of base pair length and is not limited by the deficiencies associated with gel based separation methods.

Matched Ion Polynucleotide Chromatography, as used herein, is defined as a process for separating single and double stranded polynucleotides using non-polar separation media, wherein the process uses a counter-ion agent, and an organic solvent to release the polynucleotides from the separation media. MIPC separations can be complete in less than 10 minutes, and frequently in less than 5 minutes.

The MIPC separation process differs from the traditional HPLC separation processes in that the separation is not achieved by a series of equilibrium separations between the mobile phase and the stationary phase as the liquids pass through the column. Instead, the sample is fed into the column using a solvent strength which permits the sample dsDNA to bind to the separation media surface. Strands of a specific base pair length are removed from the stationary phase surface and are carried down the column by a specific solvent concentration. By passing an increasing gradient of solvent through the sample, successively larger base pair lengths are removed in succession and passed through the column.

Descriptions of the use of MIPC, such as U.S. Pat. Nos. 5,585,236 to Bonn; 5,795,976 to Oefner; and U.S. patent application Nos. 09/183,123 to Gjerde filed Oct. 30, 1998; and 09/183,450 to Gjerde filed Oct. 30, 1998, disclose separations of dsDNA having lengths less than about 1000–2000 base pairs. The limitation in the upper range of DNA length amenable to the technique has impeded the use of MIPC in the purification of fragments larger than 2000 bp, such as those routinely used in cloning procedures, for example.

A reliable way to detect mutations is by hybridization of the putative mutant strand in a sample with the wild type strand (Lerman, et al., *Meth. Enzymol.*, 155:482 (1987)). If a mutant strand is present, then two homoduplexes and two heteroduplexes will be formed as a result of the hybridization process. Hence separation of heteroduplexes from homoduplexes provides a direct method of confirming the presence or absence of mutant DNA segments in a sample.

As the use and understanding of MIPC developed, it was discovered that when MIPC analyses were carried out at a partially denaturing temperature, i.e., a temperature sufficient to denature a heteroduplex at the site of base pair mismatch, homoduplexes could be separated from heteroduplexes having the same base pair length (U.S. Pat. No. 5,795,976; Hayward-Lester, et al., *Genome Research* 5:494 (1995); Underhill, et al., *Proc. Natl. Acad. Sci. USA* 93:193 (1996); Doris, et al., DHPLC Workshop, Stanford University, (1997)). These references and the references contained therein are incorporated herein in their entireties. Thus, the use of Denaturing HPLC (DHPLC) was applied to mutation detection (Underhill, et al., *Genome Research* 7:996 (1997); Liu, et al., *Nucleic Acid Res.*, 26;1396 (1998)).

The application of the Matched Ion Polynucleotide Chromatography (MIPC) under the partially denaturing conditions used for separating heteroduplexes from homoduplexes in mutation detection is hereafter referred to as DMIPC. In DMIPC, precise temperature control is required for maintaining both mobile and stationary phases at a partially denaturing temperature, that is, a temperature at which mismatched DNA present at the mutation site of a heteroduplex strand will denature but at which the matched DNA will remain bound into the double strand.

The hybridization process creates two homoduplexes and two heteroduplexes. Ideally, at an optimal temperature, the appearance of four distinct peaks is observed upon DMIPC analysis. DMIPC can separate heteroduplexes that differ by as little as one base pair. However, in some cases separations of homoduplexes and heteroduplexes are poorly resolved (e.g., as described by Liu et al. *Nucleic Acids Res.* 26: 1396–1400 (1998)). The presence of mutations may even be missed entirely. In some mutation analyses, only two peaks or partially resolved peak(s) are observed in DMIPC analysis. The two homoduplex peaks may appear as one peak or a partially resolved peak and the two heteroduplex peaks may appear as one peak or a partially resolved peak. In some cases, only a broadening of the initial peak is observed under partially denaturing conditions.

There is a need for improving the resolution of DNA fragments separated by MIPC, and for extending the range of base pairs which can be separated by this method. There is also a need for improving the resolution of heteroduplex and homoduplex DNA fragments using DMIPC.

SUMMARY OF THE INVENTION

It is an object of the present invention to provide a MIPC separation column which gives improved separation of polynucleotides; which allows separation of polynucleotides having lengths greater than about 1000; and which gives improved separation of homoduplex and heteroduplex DNA under partially denaturing conditions.

In one aspect, the invention concerns an improved separation column for separating a mixture of double stranded DNA fragments by Matched Ion Polynucleotide Chromatography (MIPC). The mixture contains fragments having lengths exceeding about 1000 base pairs. The column includes a cylinder having an ID greater than about 5 mm and containing polymer beads. The beads have an average diameter of 1 to 100 microns and are unsubstituted polymer beads or are polymer beads substituted with a hydrocarbon moiety having from 1 to 1,000,000 carbons. The preferred beads are characterized by being substantially free from multivalent cations which are free to bind with DNA. In one embodiment, the column ID is greater than about 7 mm. In another embodiment, the column ID is greater than about 10 mm. In yet another embodiment, the column ID is greater than about 50 mm. In still another embodiment the column ID is in the range of about 5 mm to about 1 m.

In another aspect, the invention concerns an improved method for separating a mixture of double stranded DNA fragments by MIPC in which the mixture includes fragments having lengths exceeding about 1000 base pairs. The method includes a first step (a) of applying a solution of the DNA fragments fragments and counterion reagent to separation beads. The beads are retained within a separation column. The column has an ID greater than about 5 mm. The beads have an average diameter of 1 to 100 microns, and are composed of unsubstituted polymer beads or polymer beads substituted with a hydrocarbon moiety having from 1 to 1,000,000 carbons. The preferred beads are characterized by being substantially free from multivalent cations which are free to bind with DNA. Step (b) involves eluting the fragments with a gradient of eluting solvent of increasing organic component concentration containing a counterion agent. During the elution, surfaces which are contacted by the solution of the fragments and the eluting solvent are materials which do not trap or release multivalent metal cations therefrom. The eluting is carried out under conditions effective to at least partially denature the heteroduplexes and where the eluting results in the separation of the heteroduplexes from the homoduplexes. In one embodiment of this aspect, the column ID is greater than about 7 mm. In another embodiment, the column ID is greater than about 10 mm. In yet another embodiment, the column ID is greater than about 50 mm. In still another embodiment the column ID is in the range of about 5 mm to about 1 m.

In yet another aspect, the invention concerns an improved method for separating heteroduplex and homoduplex DNA molecules in a mixture. The method includes a first step (a) of applying a solution of the fragments and counterion reagent to separation beads, said beads retained within a separation column having an ID greater than about 5 mm. The beads have an average diameter of 1 to 100 microns. The beads are unsubstituted polymer beads or polymer beads substituted with a hydrocarbon moiety having from 1 to 1,000,000 carbons. The preferred beads are characterized by being substantially free from multivalent cations which are free to bind with DNA, said column having an ID greater than about 5 mm. In step (b), fragments are eluted with a gradient eluting solvent of increasing organic component concentration containing a counterion agent. During the elution, the surfaces which are contacted by the solution of the fragments and the eluting solvent are materials which do not trap or release multivalent metal cations therefrom. The eluting is carried out under conditions effective to at least partially denature the heteroduplexes and where the eluting results in the separation of the heteroduplexes from the homoduplexes. In one embodiment of this aspect, the column ID is greater than about 7 mm. In another embodiment, the column ID is greater than about 10 mm. In yet another embodiment, the column ID is greater than about 50 mm. In still another embodiment the column ID is in the range of about 5 mm to about 1 m.

In still another aspect, the invention concerns an improved separation column for separating heteroduplex and homoduplex DNA molecules in a mixture, by Denaturing Matched Ion Polynucleotide Chromatography (DMIPC). The DNA molecules in the mixture consist of fragments having equal lengths. The column includes a cylinder having an ID greater than about 5 mm and containing polymer beads. The beads have an average diameter of 1 to 100 microns and are unsubstituted polymer beads or are polymer beads substituted with a hydrocarbon moiety having from 1 to 1,000,000 carbons. The preferred beads are characterized by being substantially free from multivalent cations which are free to bind with DNA. In one embodiment, the column ID is greater than about 7 mm. In another embodiment, the column ID is greater than about 10 mm. In yet another embodiment, the column ID is greater than about 50 mm. In still another embodiment the column ID is in the range of about 5 mm to about 1 m.

DETAILED DESCRIPTION OF THE INVENTION

This invention concerns an improved separation column. The column can be used in an MIPC as described herein. The MIPC system provides automated options for sample selection, mobile phase gradient selection and control, column and mobile phase temperature control, and fragment collection for a wide variety of MIPC separation processes. As described in earlier, copending and commonly assigned U.S. Patents or Patent Applications (U.S. Pat. Nos. 5,772,889; 5,997,742; 5,972,222; 5,986,085; U.S. patent applications Ser. Nos. 09/183,123 filed Oct. 30, 1998; 09/350,737 filed Jul. 9, 1999; 09/080,547 filed May 18, 1998; 09/318,407 filed May 25, 1999; 09/469,551 filed Dec. 22, 1999, each of which is incorporated by reference in its entirety herein) MIPC separation processes can be applied to effect size-based separation of DNA fragments, mutation detection, DNA fragment purification, PCR process monitoring, and other novel processes.

The term polynucleotide is defined as a linear polymer containing an indefinite number of nucleotides, linked from one ribose (or deoxyribose) to another via phosphoric residues. The present invention can be used in the separation of double- or single-stranded DNA or RNA. For purposes of simplifying the description of the invention, and not by way of limitation, the separation of double-stranded DNA will be described in the examples herein, it being understood that all polynucleotides are intended to be included within the scope of this invention.

Figure 1:
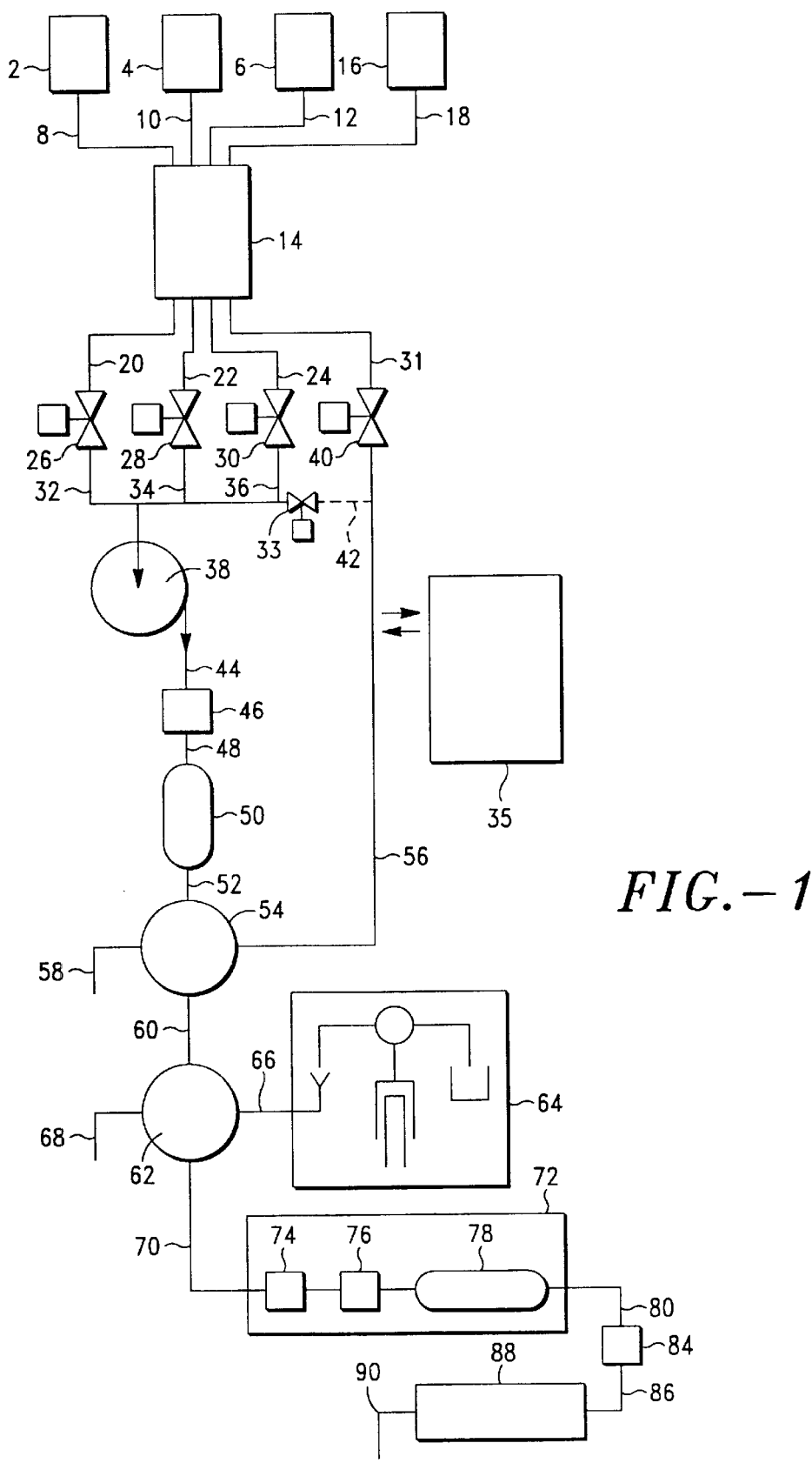
FIG. 1 is a schematic representation of a single column MIPC system using valves and valve controls to establish elution solvent gradients.

FIG. 1 is a schematic layout of the system in accordance with one embodiment of the present invention. A plurality of containers can be used as reservoirs for solutions, such as solvents, counter-ions, and other solutions, which make up the mobile phase. For example, container 2 can contain an aqueous component of a mobile phase such as an aqueous solution of counter ion agent (e.g., triethylammonium acetate (TEAA)), and container 4 can contain an aqueous solution of counterion agent plus organic (driving) solvent (e.g., TEAA plus acetonitrile). An auxiliary liquid (e.g., a co-solvent) can be held in container 6. These solutions are mixed to achieve a selected concentration of organic solvent in the mobile phase during a separation. Other examples of these solutions are provided in the Examples herein and in the commonly assigned patent indicated hereinabove. The containers have respective transport tubing such as counter-ion solution transport tubing 8, solvent solution transport tubing 10, and auxiliary liquid transport tubing 12 communicating therewith, and leading to degasser 14.

The degasser 14 removes dissolved gases from the liquids. An example of a suitable degasser is the Degassit Model 6324. Removal of dissolved oxygen is particularly important because its presence increases the risk of oxidizing ferrous or other oxidizable metals in the system components and thus introducing the corresponding cations into the mobile phase liquid.

Figure 2:
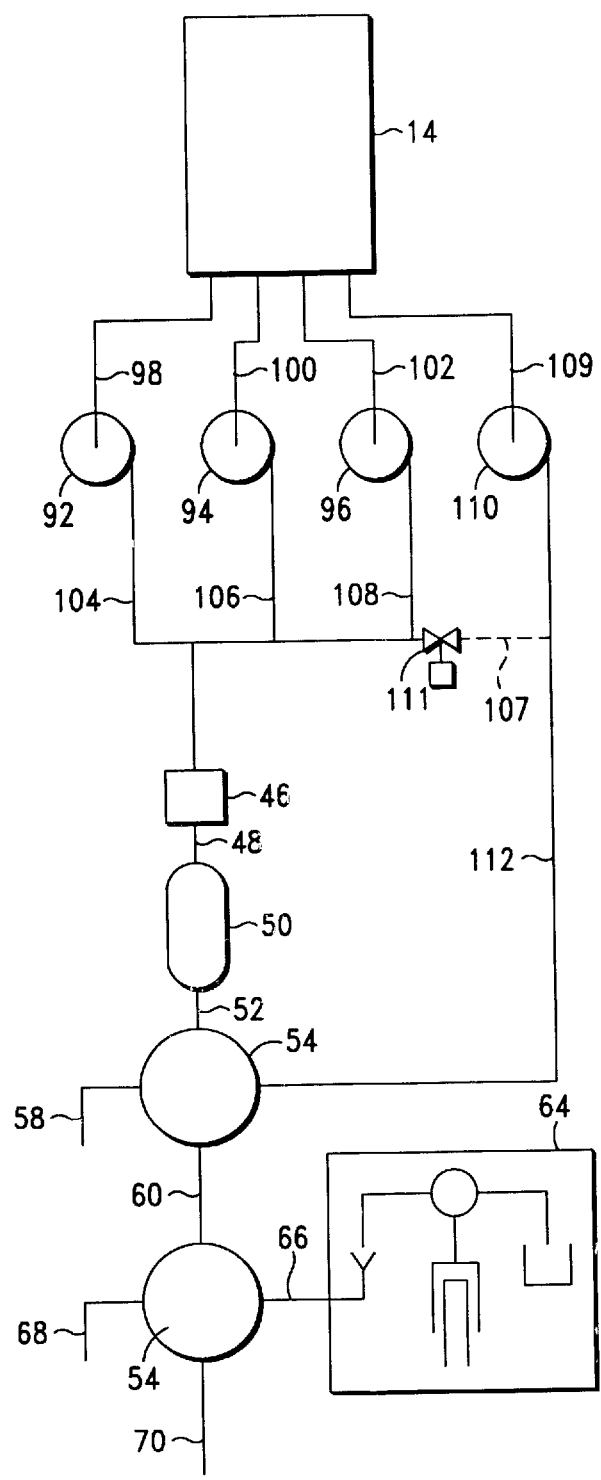
FIG. 2 is a partial schematic representation of a pump system for establishing elution solvent gradients.

Column cleaning solution is contained in cleaning solution container 16 which likewise has a cleaning solution transport conduit 18 communicating therewith leading to the degasser 14. In this embodiment, the cleaning solution can flow by gravity pressure if the container 16 is elevated above the degasser and injection valve 54. Alternatively, a pump 110 as shown in FIG. 2 can be provided to achieve cleaning solution flow.

The system of the invention incorporates conventional mobile phase flow control means which controls flow of solvent solution and aqueous components of a mobile phase. In one embodiment, the mobile phase flow control means comprises a set of flow control valves, each with automatic opening controls under computer control as described hereinbelow. In another embodiment the mobile phase flow control means comprises a set of pumps, the flow setting of which are responsive to computer control as described hereinbelow The system illustrated in FIG. 1 utilizes one embodiment of a mobile phase flow control means which includes a set of flow control valves. Degassed counterion solution conduit 20, degassed solvent solution conduit 22, and degassed auxiliary liquid conduit 24 leading from the degasser 14 communicate with respective aqueous component proportioning valve 26, solvent solution proportioning valve 28, and auxiliary liquid proportioning valve 30. The settings for these proportioning valves are set and changed by valve operators such as stepper motors associated therewith, and these valve operators respond to establish a desired set of settings in response to commands from the mobile phase flow control software module described in greater detail hereinbelow. The flow control valves 26, 28, and 30 comprise an embodiment of a mobile phase flow control means which controls the flow of solvent solution and other components of the mobile phase. The settings for these valves control the ratio of liquids (co-solvents, solvent solution, etc.) through the injector valve and the separation column. Conduits 32, 34, and 36 lead from respective proportioning valves 26, 28 and 30 to the intake of pump 38.

The cleaning solution transport conduit 31 leads to a cleaning solution valve 40. An optional cleaning solution conduit 42 leads from the valve 40 and communicates with the inlet of pump 38. Valve 33 controls flow through conduit 42.

The openings of valves 26, 28 and 30 accurately set the relative ratios of the organic solvent, and other components, within the mobile phase, a most important part of this system because the size-based DNA separation by MIPC is a function of solvent concentration. As will be described in regard to the various DNA fragment separation processes, the slope of the organic solvent gradient as a function of time is changed during the separation process, and the most critical phase may require a very precise gradient, or for some processes, a highly precise isocratic (constant solvent concentration) composition. The settings of the valves 26, 28 and 30 are established by conventional valve actuators which can be remotely set by signals to a conventional valve control device.

In a preferred embodiment, the separation system is under computer control as represented at 35. The computer includes Instrument Control Software, such as described in U.S. patent application Ser. No. 09/469,551, which provides computer controlled instructions for establishing the settings of valves 26, 28 and 30 to precise flow values at appropriate times during the operation of the system.

In a similar manner, the Instrument Control Software of the instant invention provides computer controlled instructions to establish the operational parameters of the pump 38, such as the off/on status of the pump and the pressure or flow rate settings of the pump.

Pump outflow conduit 44 communicates with the in-line mixer 46, directing the liquid flow through the mixer 46 for thorough mixing of the components. Mixed liquid outflow conduit 48 communicates with optional guard column 50 to treat the mixed liquid to remove multivalent metal cations and other contaminants which would interfere with the separation of DNA fragments. Guard column 50 can contain a cation exchange resin in sodium or hydrogen form for removal of multivalent metal cations by conventional ion exchange. Conduit 52 communicates with the outlet of the guard column and an inlet port of a cleaning solution injector valve 54. Cleaning solution supply conduit 56 connects valve 40 with the cleaning solution injector valve 54, and waste outlet conduit 58 leads to waste. Conduit 60 leads from valve 54 to the sample injection valve 62.

Sample aliquot selector 64 communicates with injector valve 62 through sample conduit 66. Waste conduit 68 leads from the injector valve and removes waste liquids.

In the injector valve 62, the sample is introduced into a stream of solvent and carrier liquid passing through the valve from conduit 60. Sample conduit 70 communicates with an outlet port of injector valve 62 and with the column prefilter 74 in the air bath oven 72. The capillary tubing coil 76 communicates with the prefilter 74 and the inlet of separation column 78. The extended length of the capillary coil 76 allows ample heat to pass from the heated oven air into the liquid passing through the coil, bringing the liquid within ±0.05° C. of a selected temperature. The oven 72 establishes this temperature uniformity in the prefilter 74, coil 76, and separation column 78.

The separation column 78 is packed with beads having a unique separation surface which effects a size-based separation of DNA fragments in the presence of a counter-ion by the MICP process. The separation process and details about the column and beads are described in detail hereinbelow. A stream of mobile phase containing base pair length size-separated DNA fragments passes from the separation column 78 through conduit 80.

Conduit 80 communicates with a detector 84. The detector can be a conventional UV absorbance device which measures the UV absorbance of the DNA fragment structures in the liquid mobile phase. The absorbance is a function of the concentration of the DNA fragments in the liquid being tested.

Alternatively, if the DNA is labeled with a fluorescent marker, the detector can be a fluorescence detector which can continuously measure the level of the fluorescent marker in the liquid by detecting the emission level at the frequency most appropriate for the marker. It will be readily apparent that any detecting system capable of continuously measuring a characteristic of the liquid which is a function of the concentration of the DNA fragments therein is suitable and intended to be within the scope of this invention. Examples of suitable detectors include the L-7420 UV-Vis detector, and the L-7480 Fluorescence detector available from Hitachi. The electrical output from the detector preferably is converted to a digital form by an A/D converter and recorded in standard digital format to a digital storage device such as a disk drive in computer 35. Conduit 86 removes the tested liquid.

Then, the mobile phase passes to the fragment collector 88 where selected portions of the mobile phase containing a separated DNA fraction are collected in vials for later processing or analysis. Uncollected fractions are removed through waste conduit 90.

The DNA separation process is impaired by the presence of multivalent cations. In the above description, the liquid flow system is described as a series of conduits. The conduits are capillary tubing selected to avoid introduction of multivalent cations into the liquids. The preferred capillary tubing materials are titanium and PEEK. For similar reasons, the other components of the system are preferably made of titanium or PEEK or have the surfaces exposed to the liquid coated with PEEK to protect them from oxidation and prevent the introduction of multivalent cations into the liquid. Stainless steel can also be used provided it has been treated to remove all oxidized surface materials and the solutions contacting the stainless steel surfaces are free of dissolved oxygen.

Illustrating another embodiment of a mobile phase flow control means, FIG. 2 is a partial schematic representation of a pump system for establishing mobile phase composition. This system relies on proportioning pumps to control the ratio of aqueous component and solvent solution, such as solutions A and B described hereinabove. The inlets of proportioning pumps 92, 94 and 96 by way of their respective supply conduits 98, 100, and 102 communicate with the degasser 14, and by way of their respective outlet conduits 104, 106 and 108 communicate with the inline mixer 46. The operational speed for these proportioning pumps are calibrated to flow rates therethrough and are controlled by a flow control software module described in greater detail hereinbelow. The settings for these proportioning valves control the liquid flow speed and the ratio of liquids (co-solvents, driving solvents, etc.) through the injector valve and the separation column.

A pump 110 can supply cleaning solution to the system through optional conduit 112. An optional conduit 107 leads from conduit 112 and communicates with the in-line mixer 46. Valve 111 controls flow through conduit 107.

Examples of suitable mobile phase control means for use in the invention include the programmable dual piston pump Model L-7100 available from Hitachi and the Model 2690 Separations Module available from Waters.

Figure 3:
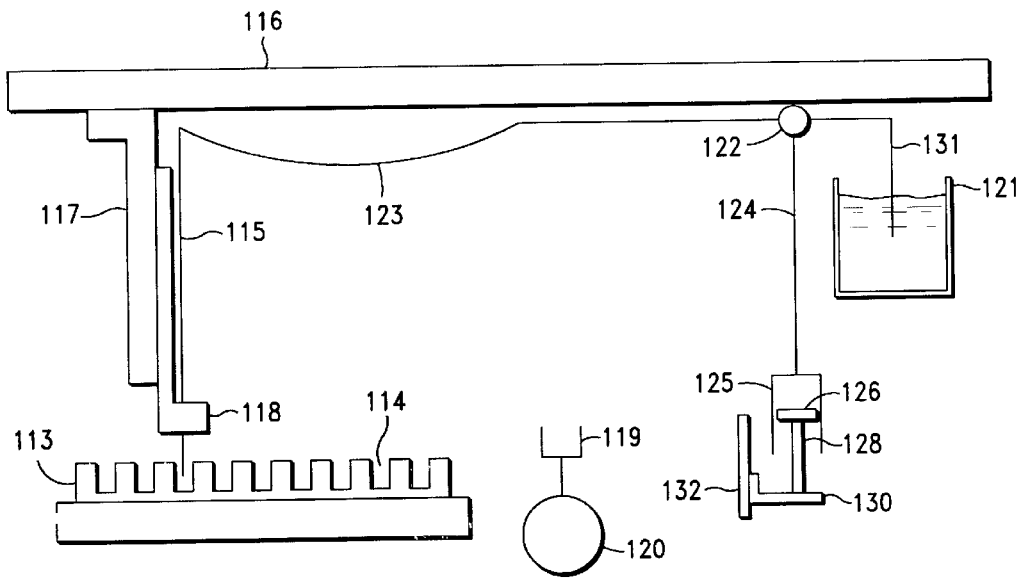
FIG. 3 is a schematic representation of an autosampler subsystem.

FIG. 3 is a schematic representation of an autosampler subsystem used in the MIPC system. This autosampler removes an aliquot having a predetermined volume from a selected well or vial (e.g., micro-centrifuge tube) supported in a multi-well 113. Microwell plates can have any predetermined number of wells 114 having a precise dimensional position for each well, such as the standard 96 well multiwell plate. The sampling needle 115 is supported on a sampling carriage 116. The sampling carriage 116 has a needle support 118 mounted for vertical movement on vertical support 117. Vertical support 117 is mounted for lateral movement on carriage 116. Lateral movement of the support 117 positions the needle above a selected well or the injector port 119 of injection valve 120. The flexible tubing 123 is mounted in sealed engagement with the needle 115 at one end and with the syringe needle 124 at the other end. The syringe needle 124 communicates with the inner volume of the syringe cylinder 125. The piston 126 is mounted on the syringe actuator rod 128 and forms a sealed engagement with the inner wall of the cylinder 125. In operation, vertical upward movement of the syringe actuator rod 128 displaces liquid in the cylinder 125, and vertical downward movement of the syringe actuator rod 128 pulls liquid into the syringe. Rod 128 is attached to clamp 130 which is supported for movement along guide element 132. When valve 122 is positioned to provide communication between the needle 124 and the tubing 123, the downward movement of the piston 126 pulls sample into the needle 115 from a well 114. When needle 115 is positioned above injector valve port 119, upward movement of the piston 126 discharges sample from needle 115 into port 119.

Conduit 131 extends from valve 122 to the cleaning solution reservoir 121. When valve 122 is in the position providing communication between the needle 124 and the conduit 131, the downward movement of the piston 126 draws cleaning solution into the needle. When the needle 115 is positioned above the injector port 119 and valve 122 is positioned to provide communication between the needle 124 and the conduit 123, upward movement of the piston 126 discharges cleaning solution into the injector port 119. Examples of suitable autosamplers include the HITACHI Model L-7250 Programmable Autosampler and the HTS PAL High Throughput Autosampler (Shimadzu, Columbia, Md.).

Figure 4:
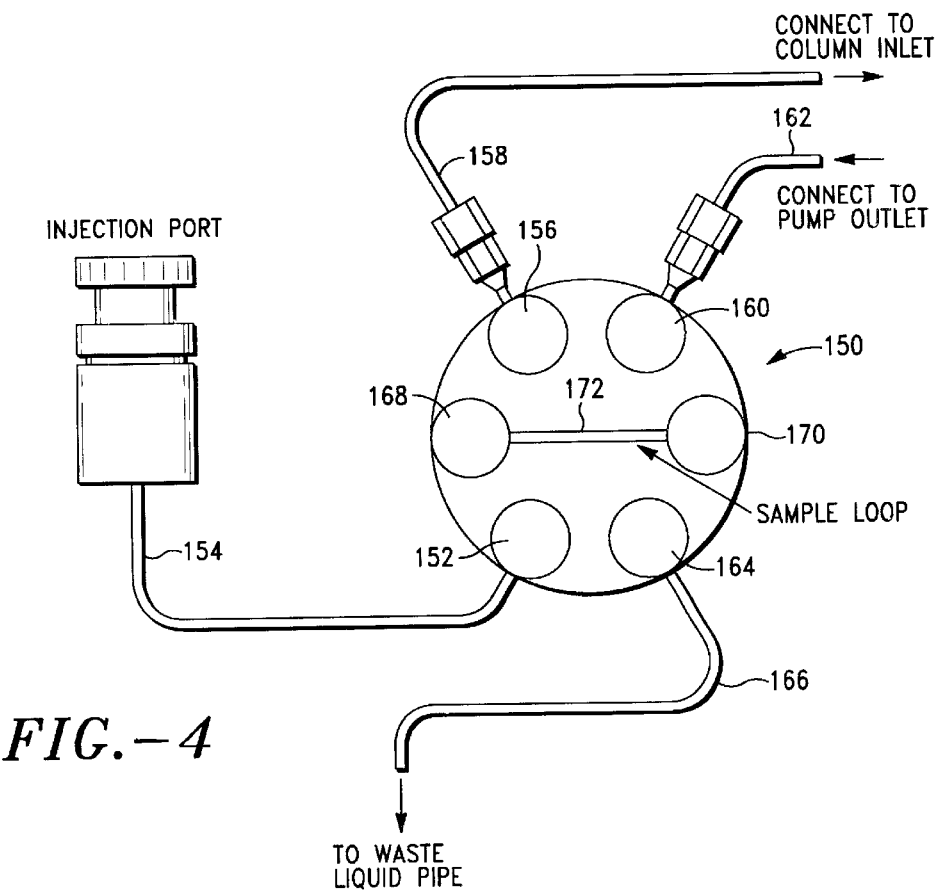
FIG. 4 is a schematic representation of an injection valve used in the MIPC system.

FIG. 4 is schematic representation showing the structure of the sample injection valve and cleaning solution injection valve for use in the MIPC system. The same valve structure can be used for both the sample injection and cleaning solution injection. The injection valve 150 is a six-port, rotary valve operated by a conventional valve motor such as a stepper motor (not shown). Exemplary valves include the LabPRO valves available from RHEODYNE (Cotati, Calif.). The valve has six external ports permanently connected to inlet and outlet conduits. External port 152 is connected with an injection line 154 for receiving a sample to be analyzed. External port 156 is connected with a column supply conduit 158 communicating with the separation column 78 (FIG. 1). External port 160 is connected with an inlet conduit 162 communicating with the outlet of pump 38 (FIG. 1). External port 164 is connected with a waste conduit 166. Opposed outlet ports 168 and 170 communicate with the opposed sample inlet and outlet ends of a sample loop 172. During the injection of cleaning solution, the valve injects a block of cleaning solution into the solvent stream, regenerating and cleaning the separation column and other components downstream of the injection, removing from the surfaces accumulated residues and any residual DNA remaining from prior separations.

The connections between the external ports and internal passages, and their operation in the cleaning solution injector valve 54 and sample injector valve 62 in FIG. 1 is described in FIGS. 5–8. The description hereinbelow is presented for the sample injection valve 62, but the same relationships and operation apply to the cleaning solution injection valve with the exception of the liquids being injected and their source.

Figure 5:
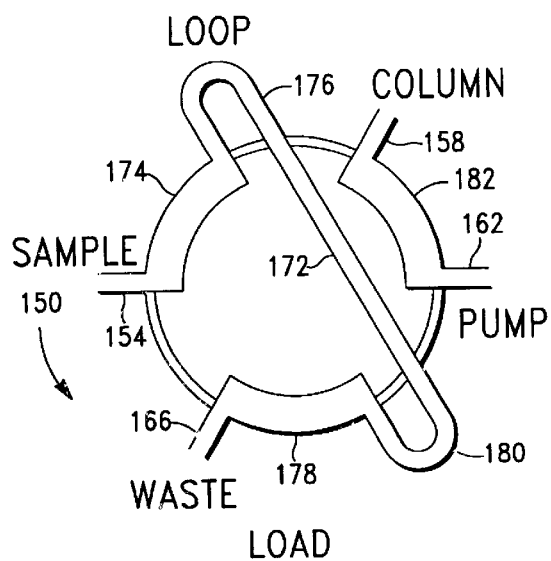
FIG. 5 is a schematic representation of an injection valve in the filled loop load position.
Figure 6:
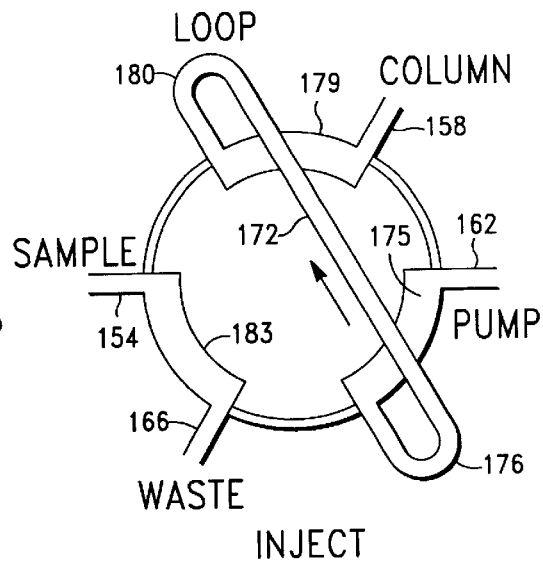
FIG. 6 is a schematic representation of an injection valve in the filled loop injection position.
Figure 7:
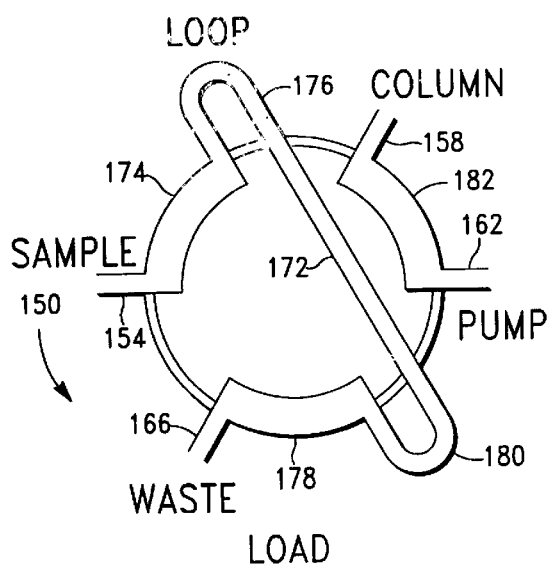
FIG. 7 is a schematic representation of an injection valve in the partial loop load position.
Figure 8:
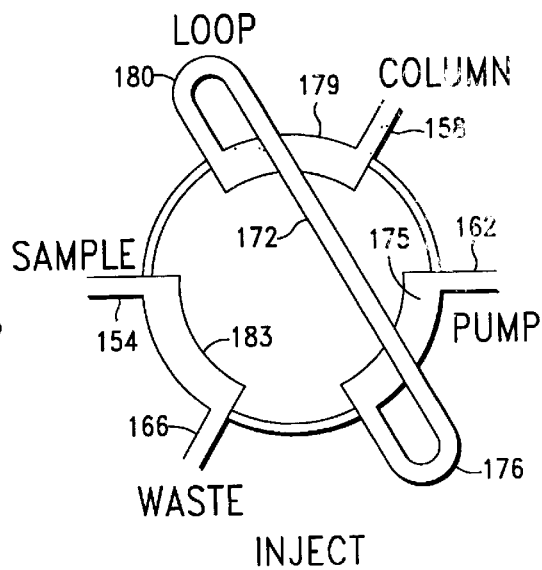
FIG. 8 is a schematic representation of the injection valve in the partial loop injection position.

FIGS. 5 and 6 describe the use of the valve for filled loop injection, the mode used when a larger volume of sample (or cleaning solution) is to be injected. FIG. 5 is a schematic representation of an injection valve in the sample load position, and FIG. 6 is a schematic representation of the injection valve in the injection position. In the load position shown in FIG. 5, a first internal passageway 174 of the valve connects the first end 176 of loop 172 with the sample injection line 154, and a second internal passageway 178 connects the second end 180 of loop 172 with the waste conduit 166. A third internal passageway 182 connects the pump outlet conduit 162 with the conduit 158 to the separation column 78. While sample from the injection port 154 is introduced into the sample loop 172 through passageway 174, any surplus or liquid in the loop 172 is expelled to the waste conduit 166 through passageway 178. Simultaneously, mobile phase solutions flow from the pump conduit 162 to the separation column 78 through third conduit 182.

Rotation of the valve in the direction of arrow 150 to the injection position shown in FIG. 6 moves the internal passageways to establish a different set of connections with the inlet and outlet conduits. Passageway 179 connects one end 180 of the loop 172 with the conduit 158 leading to the separation column, and passageway 175 connects the other end 176 of the loop 172 with the inlet conduit 162 leading to the pump. Mobile phase solution from the pump enters passageway 175 and passes through the loop 172, expelling sample solution into the conduit 158 leading to the column and continues to rinse the loop, carrying any residue into the column conduit 158. Meanwhile, passageway 183 connects the sample injection conduit 154 to waste, permitting passage of cleaning solution, if desired, through passageway 183. This procedure provides a reliable injection of a measured volume of sample solution into the conduit leading to the separation column 78 (FIG. 1), the liquid passing through the prefilter 74 and temperature regulating coil 76 before it reaches the separation column.

The system of the invention incorporates oven temperature control means for controlling the temperature of the separation column and the mobile phase entering the column.

Figure 9:
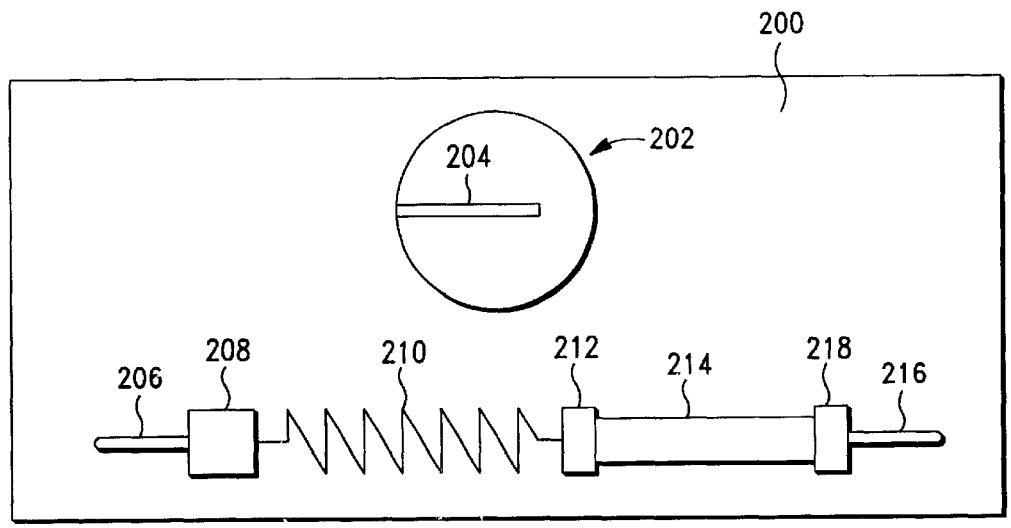
FIG. 9 is a front view of the separation compartment of an improved HPLC DNA analyzer column oven according to this invention.
Figure 10:
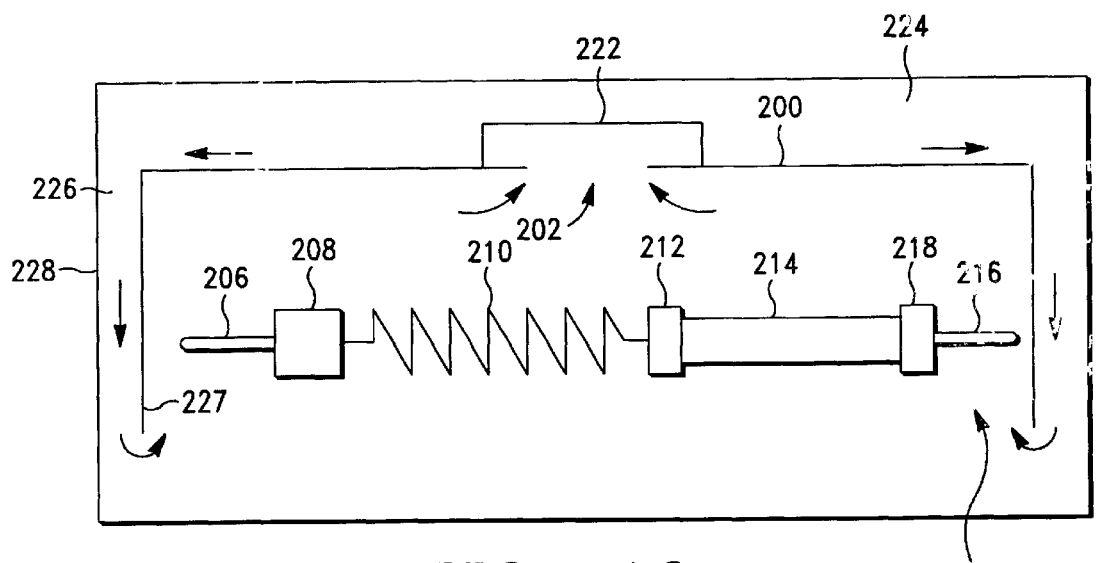
FIG. 10 is a top view of the HPLC DNA analyzer column oven shown in FIG. 9.

FIGS. 9 and 10 illustrate one embodiment of a temperature control means. FIG. 9 is a front view of the process compartment of an HPLC DNA analyzer column oven, and FIG. 10 is a top view of the HPLC DNA analyzer column oven shown in FIG. 9. The process compartment in the embodiment shown in FIGS. 9 and 10 is divided from the heating compartment by backwall 200 in which air exhaust port 202 is positioned. A metal bar 204 enclosing a temperature sensor such as a thermocouple or thermister is positioned in the port 202 to measure the temperature of the air passing through the port. Capillary tubing 206 leads from the sample injector (not shown) to a prefilter 208. Prefilter 208 is an inline filter or guard cartridge, such as described in U.S. Pat. No. 5,772,889, which removes contaminants from the incoming liquid. An elongated coil 210 of capillary tubing has an inlet end in communication with prefilter 208 for receiving mobile phase liquid therefrom. The elongated coil 210 has an outlet end communicating with the inlet end 212 of a separation column 214. Separation column 214 preferably contains MIPC separation media. Outlet tubing 216 leads from the outlet end 218 of the separation column 214 to detector 84 (FIG. 1). Coil 210 is a liquid heating coil made of a DNA compatible, multivalent cation free tubing such as titanium or PEEK. The length and diameter of tubing used is any length which is sufficient to enable liquid mobile phase passing therethrough to reach the equilibrium temperature of air in the processing compartment. A tubing length of from 6 to 400 cm and a tubing ID of from 0.15 to 0.4 mm is usually sufficient. Since the length of tubing 210 does not degrade the separation of components achieved by the system, the length can be selected based on the length required to achieve effective heating of the process liquids.

Referring to FIG. 10, air from the processing compartment 220 passes through the opening 202 in wall 200, through a heater/fan system 222 for temperature adjustment. The adjusted air received by the heating compartment 224 recycles back to the processing compartment 220 along the passageways 226 defined by the spacing between the sidewalls 227 and the outer oven wall 228. The heating coil in the embodiment shown in FIGS. 9 and 10 provides a temperature accuracy to within the range of ±0.2° C. and reduces the temperature equilibrium time between temperature settings to below 5 minutes for temperature changes of 5° C. and below 2 minutes for temperature changes of up to 1° C.

Figure 11:
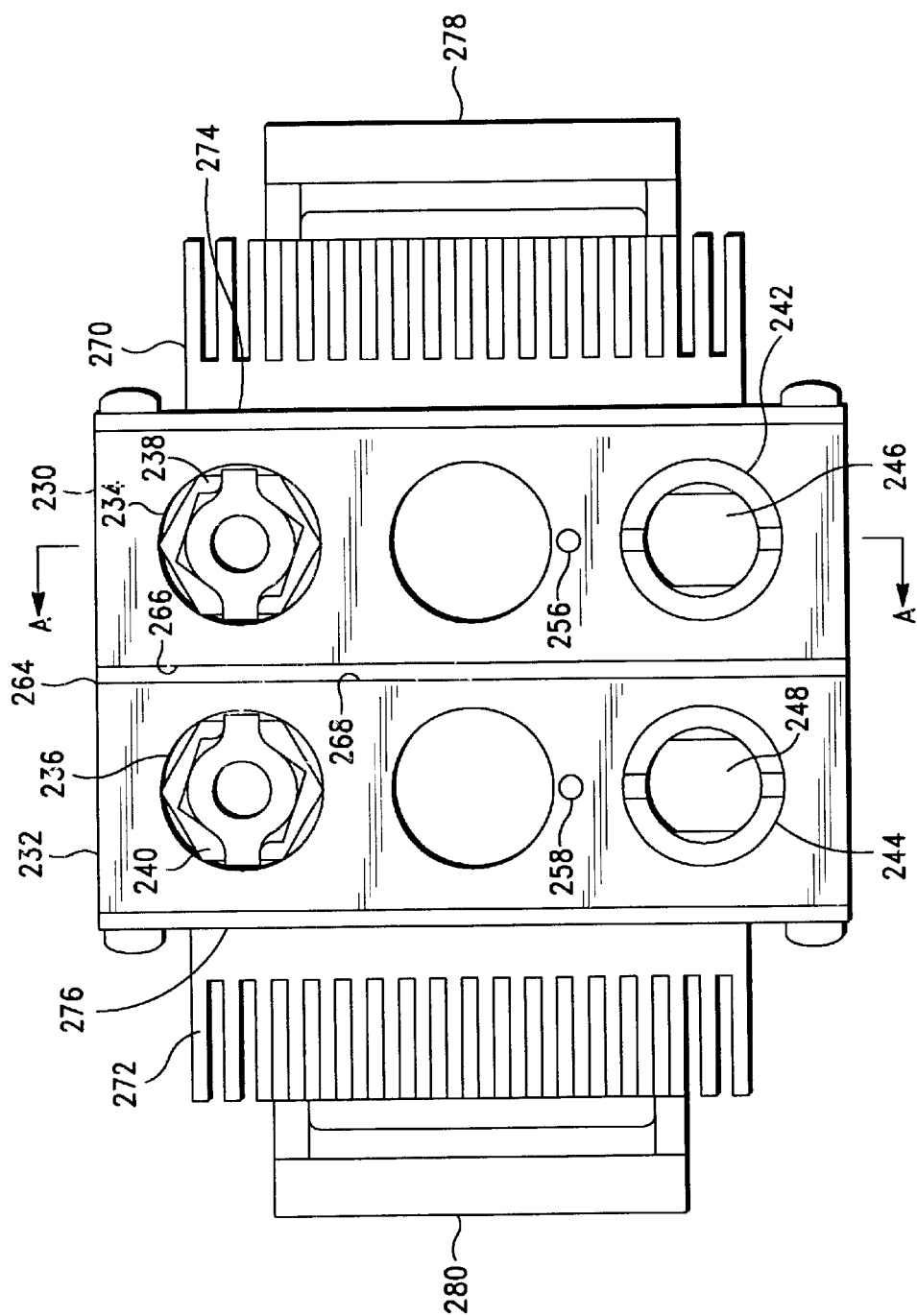
FIG. 11 is an end view of the compact column heater embodiment of this invention.
Figure 12:
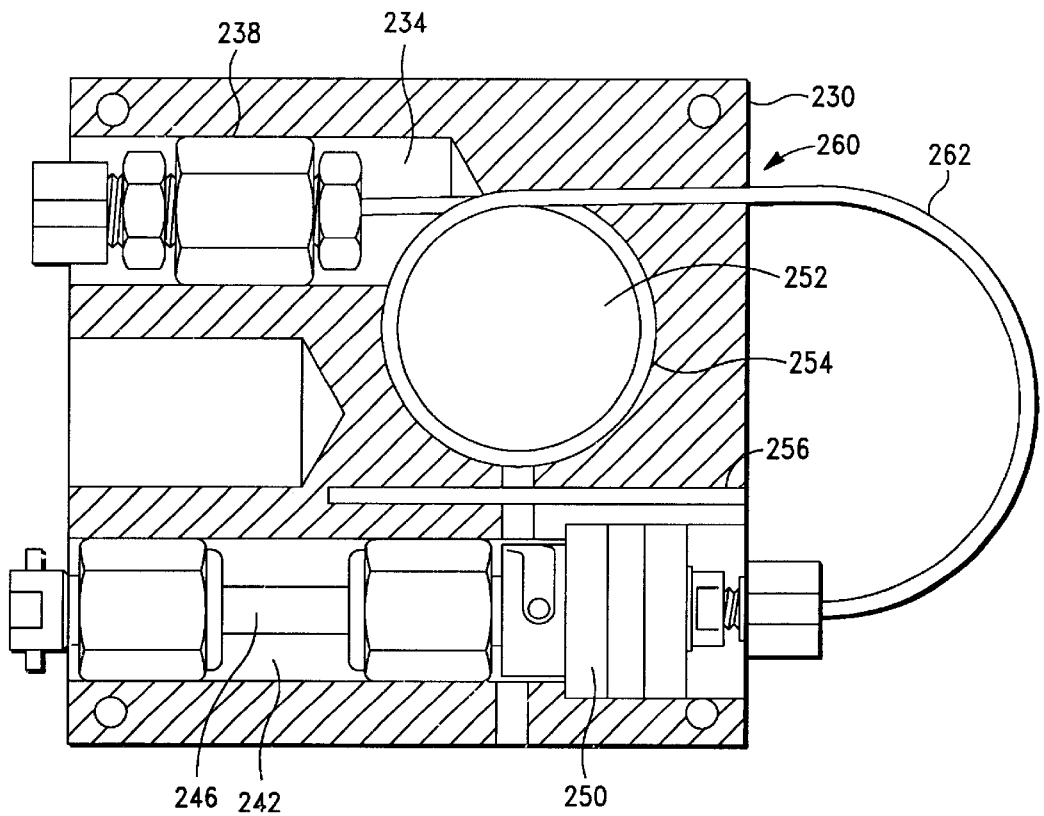
FIG. 12 is a cross-sectional view taken along the line A—A in FIG. 11.

FIGS. 11 and 12 illustrate another embodiment of a temperature control means. FIG. 11 is an end view of a compact column heater, and FIG. 12 is a cross-sectional view taken along the line A—A in FIG. 11. This embodiment relies on direct metal-to-metal conduction of heat to and from the system components and does not depend upon an air bath to achieve temperature changes and accuracy. This embodiment is shown for a two column system, although it could be used for a single column, if desired. It comprises heat conducting blocks (230,232) having receptacles sized and shaped to receive the system components. Filter cavity or prefilter receptacles (234,236) have inner surfaces which are sized to receive prefilters (238,240) and establish heat transfer contact with the outer surfaces thereof. Separation column receptacles (242,244) have inner surfaces sized to receive respective separation columns (246,248) and separation column couplers (250) (one is shown in FIG. 12) which connect capillary tubing to the respective separation columns. Receptacles (242,244) are sized and shaped to establish heat transfer contacts between the inner heat transfer surfaces of blocks (230,232) and the separation column components received therein. Capillary coil receptacles 252 (one is shown in FIG. 12) have an inner surface which is shaped to receive a coils of capillary tubing 254 (one is shown in FIG. 12) and to establish heat transfer contact with the outer surface thereof. In the embodiment shown in these figures, receptacles (234,236) and (242,244) can be cylindrical holes with approximately parallel central axes lying in a common plane. It would be readily apparent to a person skilled in the art that other configurations are equally suitable and all configurations are considered to be within the scope of this invention.

Temperature sensor receptacles (256,258) are provided in heat conducting blocks (230,232). Capillary receptacle passageways 260 for receiving connecting tubing 262 in a heat-conducting relationship are also provided in the heating-conducting block (230,232). The capillary coil receptacles 252 are shown in this figure to be cylindrical cavities with their axes perpendicular to the axes of receptacles (234,236) and (242,244). Optionally, a conductive metal cylinder (not shown) can be positioned within the capillary coils in heat conducting contact with the inner surfaces thereof to increase heat transfer area between the metal block heating assembly and the liquid in the coils. A KAPTON resistance heater or other type of heating unit 264 is positioned between and in heat-conducting contact with surfaces 266 and 268 of heating blocks (230,232) to transfer heat to the heat-conducting blocks. Heat sinks (270,272) are positioned in heat-conducting relationship with opposed cooling surfaces (274,276) of the heat conduct blocks (230, 232) to remove heat therefrom. Cooling fans 278 and 280 are in a heat removal relationship with the heat sinks 270 and 272 and are activated to accelerate heat removal therefrom.

The heat conducting blocks 230 and 232, and the heat sinks 270 and 272 are made of a material having high heat conductivity such as aluminum or copper, although they can be made of other heat-conducting solids such as ferrous metals or any other solid material having the requisite heat conductivity. Heat pipes can also be used as heat sinks.

The capillary tubing can be made of PEEK or titanium, although titanium is preferred for maximum heat transfer efficiency. With this improved heat transfer, the capillary coil can have a fully extended length as short as 5 cm although a minimum coil length of 10 cm is preferred. A longer coil of PEEK tubing would be required to achieve the same heat transfer as titanium capillary tubing.

The system shown in FIGS. 11 and 12 comprises two systems in mirror image. It will be readily apparent that for a single column, half the system would be sufficient and is intended to be included within the scope of this invention. The position, alignment and spacing of the receptacles are not a critical feature of this invention. Any alignment and configuration which provides a compact and heat-transfer efficient result is intended to be included within the scope of this invention.

The embodiments shown in FIGS. 11 and 12 provide a compact heater which is more responsive to heater controls, provides rapid changes from one temperature platform to another, and maintains a temperature accuracy within ±0.5° C. of a set temperature. The heat transfer rate obtained with the metal-to-metal contact between the heating block and the elements being heated is far greater than can be obtained in an air bath system, providing the more rapid response to a changed temperature and greater temperature accuracy. It also allows process liquid temperature adjustment with a shorter capillary tubing coil.

Figure 13:
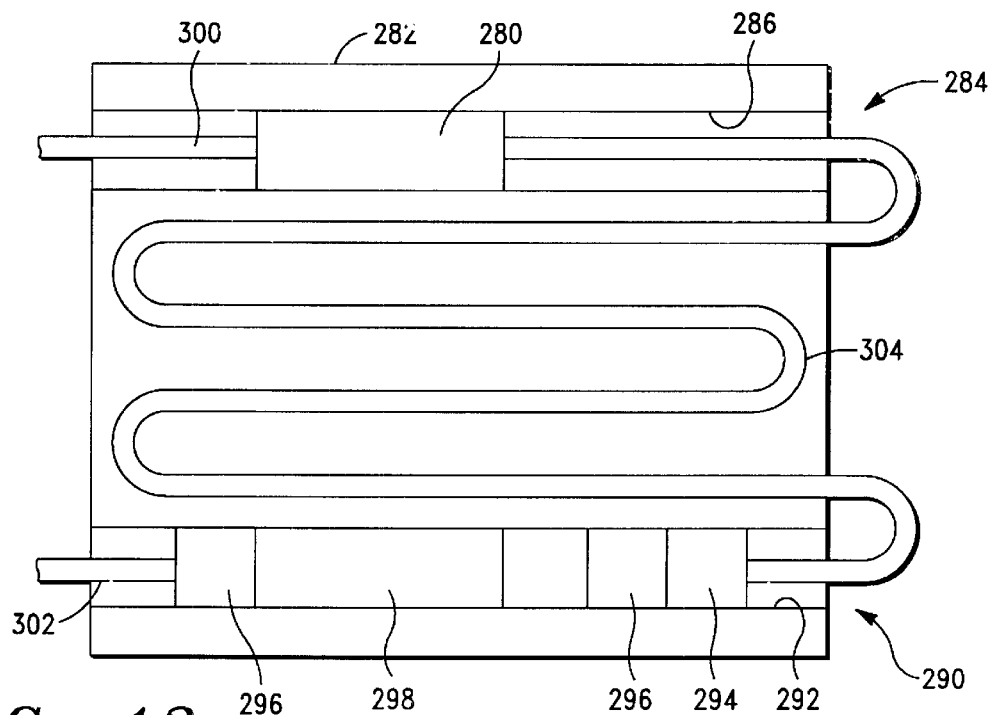
FIG. 13 is a schematic view of a Peltier heater/cooler embodiment of this invention.
Figure 14:
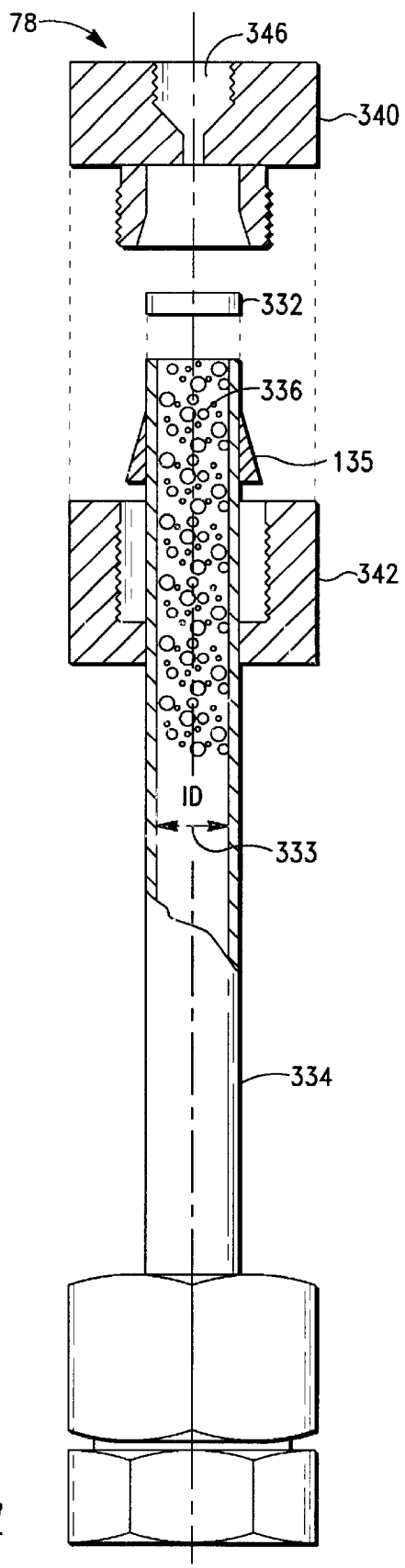
FIG. 14 is a representation of the physical structure of a representative separation column.

In yet another illustration of a temperature control means, FIG. 13 shows a schematic view of a preferred Peltier heater/cooler embodiment. Heating block 282 is in conductive contact with a Peltier heating element (not shown) for heating or cooling required to reach and maintain a desired temperature. Channel 284 is a prefilter receptor having an inner surface 286 in heat conductive relationship with prefilter 288. Channel 290 is a column and column guard receptor having an inner surface 292 in heat conductive relationship with coupler 294 and end nut elements 296 of separation column 298. Capillary tubing 300 communicates with the prefilter 288 and the sample and solution sources (not shown). Capillary tubing 302 from the outlet of the separation column 288 communicates with an analyzer 84 (FIG. 1). Capillary tubing 304 connects the outlet end of the prefilter 288 with the coupler 294, which in turn communicates with the separation column 298. Capillary tubing 304 is received in a labyrinth-like configuration of channels in the heating block 282 to provide increased capillary length and surface contact between the capillary tubing 304 and the heating block 282. The configuration of the labyrinth and tubing can be any configuration which provides an adequate capillary length and surface contact, including additional loops and capillary placement of more than one pass per channel. The capillary tubing 304 can be PEEK or titanium, titanium being preferred because of its high heat conductivity. The heating block 282 can be any heat conductive metal. Aluminum or copper are preferred because of their higher heat conductivity, although ferrous metals such as steel can be used. The Peltier heater is controlled with a conventional temperature and control system (not shown) such as the systems used in Peltier thermocyclers. As with the embodiment shown in FIGS. 11 and 12, the temperature accuracy achieved by the Peltier heated block is ±0.5° C.

Features of improved air bath oven and solid block heating systems described hereinabove with respect to FIGS. 9–13 are described in greater detail in commonly owned, copending U.S. patent application Ser. No. 09/295,474 filed Apr. 19, 1999, the entire contents of which are hereby incorporated by reference.

An important aspect of the present invention concerns the cross-sectional dimension of the separation column 78. FIG. 4 is a partially exploded representation of the physical structure of a representative separation column. The column comprises a cylinder or tube 334 with external ferrule 335 on both ends. The tube has internal diameter (ID) as shown at 333 and is filled with separation media 336. A porous frit 338 is held against the upper surface of the separation media by the end fitting 340. The end fitting 340 receives frit 338 and holds the frit against the end of the tube 334. The internally threaded nut 342 receives the externally threaded fitting 340 in a threaded engagement. The fitting 340 has an internally threaded end receptor 346 for receiving a capillary tubing end coupler (not shown).

The material comprising the cylinder can be polymer or metal. Stainless steel tubes suitable for use in the present invention are available commercially, for example from Isolation Technologies Inc. (Hopedale, Mass.). Examples include stainless steel tubing having ID sizes such as 4.6, 6.5, 7.8, 10.0, 21.2, 30 and 50 mm. Some separations are carried out using columns having diameters as large as 500 mm. Columns as large as 1 m are used for large-scale commercial manufacture. The column preferably includes porous frits 338 (e.g., as manufactured by Mott Corporation, Farmington, Conn.) inside the fittings on both ends and can include end seals that screw into the fittings (available from Upchurch Scientific, Oak Harbor, Wash. and/or Isolation Technologies).

The separation media 336 comprises organic polymer materials or inorganic materials having the requisite structure and non-polar surfaces. Suitable materials are described hereinbelow and in copending, commonly assigned patent applications Ser. No. 09/058,580 filed Apr. 10, 1998 and Ser. No. 09/183,123 filed Oct. 20, 1998.

In a preferred embodiment of the present invention, all of the process solution-contacting surfaces are subjected to a multivalent cation removal treatment to remove any potential source of multivalent cation contamination. These surfaces include the column inner surface, porous frits, conduits, mobile phase supply system, injector valves, mixers, pumpheads, and fittings. A non-limiting example of a multivalent cation removal treatment is an acid wash treatment. This wash treatment can include flushing or soaking and can include sonication. An example of an acid wash treatment is sonication of a titanium frit in the presence of aqueous nitric acid solution, followed by sonication in water until a neutral pH is achieved. Other treatments include contacting the surfaces with chelating agents such as EDTA, pyrophosphoric acid, or phosphoric acid (e.g. 30% by weight phosphoric acid).

Figure 15:
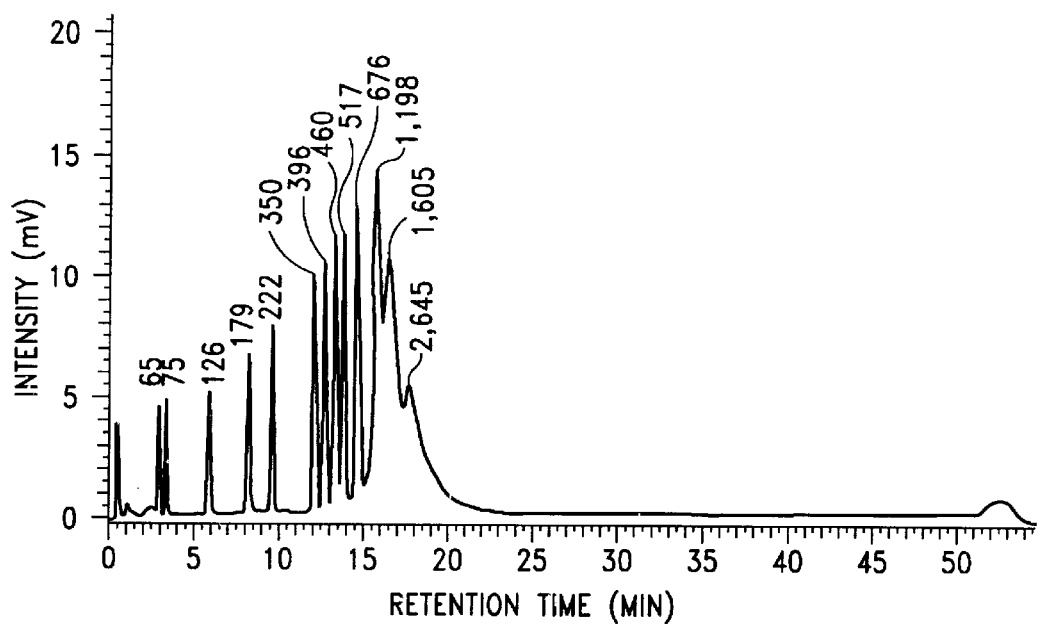
FIG. 15 is a MIPC separation of pGEM DNA markers on a 50 mm×4.6 mm ID column. Peaks are labeled with the number of base pairs of the eluted fragment.

A representative example of a size-based DNA separation is described in Example 1 (FIG. 15) in which a standard mixture of DNA fragments, pGEM® DNA Markers (Promega Corp. Madison, Wis.), was eluted using a 50 mm×4.6 mm ID column. The mixture included fragments of double stranded DNA having the base pair lengths as indicated in FIG. 15. The fragments having sizes above about 600 bp, in particular the 1,198 bp, 1,605 bp, and 2,645 bp fragments, were poorly resolved, even though the slope of the mobile phase gradient was relatively shallow (increasing at about 0.33% B/min) during the elution of these peaks.

Applicants surprisingly observed dramatic and unexpected improvement in the separation of these peaks when the separation of the pGEM mixture was conducted using a column having an ID of 7.8 mm (FIG. 16) as described in Example 2. The 1198 bp, 1605 bp, and 2645 bp fragments were clearly separated. Improved separation of dsDNA fragments having lengths exceeding 600 base pairs is obtained using columns having internal diameters greater than about 5 mm.

In other experiments, improved separation using a column having an ID of 7.8 mm was observed using DNA mixtures containing fragments ranging from about 100 to about 20,000 base pairs, as described in Examples 9 and 10.

Improved resolution during the separation of DNA by MPIC is obtained using a column having a ID of greater than 5 mm, preferably greater than about 7 mm, more preferably greater than about 10 mm. In other embodiments, improved separation is obtained with a column can having an ID within the range of about 5 mm to about 1 m.

Another aspect of the present invention concerns an improved separation column and method for use in conducting DNA mutation detection by DMIPC. As discussed hereinabove, the instant invention can be used to detect mutations in double stranded DNA. The following definitions will be used herein:

A "homoduplex" is defined herein to mean, a double stranded DNA fragment wherein the bases in each strand are complimentary relative to their counterpart bases in the other strand.

A "heteroduplex" is defined herein to mean a double stranded DNA fragment wherein at least one base in each strand is not complimentary to at least one counterpart base in the other strand. This can be due to a mismatched base or a deletion. Since at least one base pair in a heteroduplex is not complimentary, it takes less energy to separate the bases at that site compared to its fully complimentary base pair analog in a homoduplex. This results in the lower melting temperature at the site of a mismatched base of a hetroduplex compared to a homoduplex.

The term "hybridization" refers to a process of heating and cooling a dsDNA sample, e.g., heating to 95° C. followed by slow cooling. The heating process causes the DNA strands to denature. Upon cooling, the strands recombine into duplexes in a largely statistical fashion. If the sample contains a mixture of wild type and mutant DNA, then hybridization will form a mixture of hetero- and homoduplexes.

The "heteromutant site separation temperature" T(hsst) is defined herein to mean the temperature which preferentially denatures the heteroduplex DNA at a site of mutation and which gives the greatest difference in the degree of denaturation between the heteroduplexes and homoduplexes. This is a temperature which is optimal to effect a chromatographic separation of heteroduplexes and homoduplexes by DMIPC and hence, detect mutations.

The term "heteromutant" is defined herein to mean a DNA fragment containing a polymorphism or non-complimentary base pair.

The term "mutation separation profile" is defined herein to mean a DMIPC separation chromatogram which shows the separation of heteroduplexes from homoduplexes. Such separation profiles are characteristic of samples which contain mutations or polymorphisms and have been hybridized prior to being separated by DMIPC.

Figure 17:
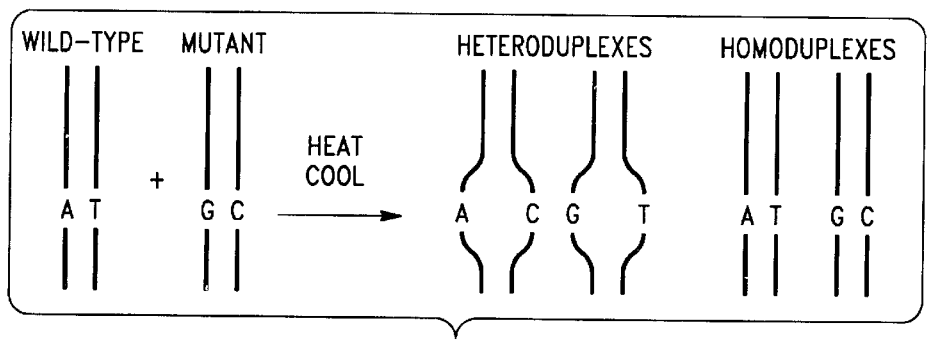
FIG. 17 shows a schematic representation of a hybridization to form homoduplex and heteroduplex.

A reliable way to detect mutations is by hybridization of the putative mutant strand in a sample with the wild type strand (Lerman, et al., Meth. Enzymol., 155:482 (1987)). If a mutant strand is present, then two homoduplexes and two heteroduplexes will be formed as a result of the hybridization process, as shown in FIG. 17. Hence separation of heteroduplexes from homoduplexes provides a direct method of confirming the presence or absence of mutant DNA segments in a sample.

Figure 18:
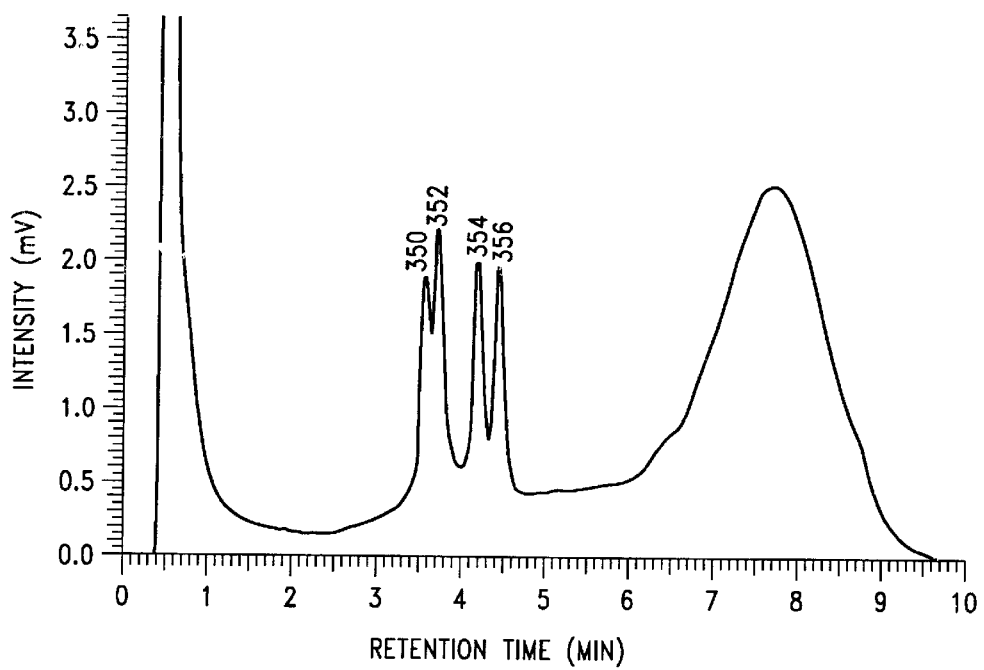
FIG. 18 is a mutation separation profile of a 209 bp homoduplex/heteroduplex mixture using a 50 mm×4.6 mm ID column.

In one example of a DMIPC analysis, a standard containing 209 base pair homoduplexes and heteroduplexes was subjected to DMIPC as shown in FIG. 18. as a series of separation chromatograms and the separation process is described in Example 4. The sample, containing a heterozygous sample of 209 base pair homoduplex fragments wherein the mutant fragments contained a single base pair deviation from the wild type, was hybridized by heating and then cooling. The hybridization process created two homoduplexes and two heteroduplexes as shown schematically in FIG. 17.

Referring to FIG. 18, and Example 3, the DMIPC analysis was performed using a separation column having an ID of 4.6 mm. There was partial overlap between the two heteroduplexes 350,352 and also between the two homoduplexes 354,356. Applicants surprisingly observed dramatic and unexpected improvement in the separation of the peaks when the separation of the 209 base pair mutation standard was conducted using a column having an ID of 7.8 mm (FIG. 19) as described in Example 4. The results demonstrated improved separation of two homoduplex fragments 350,352 from each other, the two heteroduplex fragments 354,356 from each other,.and increased separation between the homoduplex and heteroduplex pairs as indicated by distance "d".

To achieve improved peak resolution during the separation of homoduplex and heteroduplex DNA by DMPIC, the method is preferably performed using a column having a ID of greater than about 5 mm, more preferably greater than about 7 mm, most preferably greater than about 10 mm. In other embodiments, the column can have an ID within the range of about 5 mm to about 1 m.

In its most general form, the separation process used in the chromatography system of the invention concerns separation of polynucleotides, e.g. DNA, utilizing a stationary separation medium having non-polar surfaces. The preferred surfaces are essentially free from multivalent cation contamination which can trap polynucleotides. The separation is performed on the stationary surface. The surface can be porous, but preferably any surface pores are of a size which excludes the smallest polynucleotide being analyzed.

In general, the only requirement for the separation beads of the present invention is that they must have a surface that is either intrinsically non-polar or be bonded with a material that forms a surface having sufficient non-polarity to interact with a counterion agent.

The non-porous polymeric beads can have an average diameter of about 0.5–100 microns; preferably, 1–10 microns; more preferably, 1–5 microns. Beads having an average diameter of 1.0–3.0 microns are most preferred.

In U.S. Pat. No. 5,585,236, Bonn et al. had characterized the nucleic acid separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counterion agent, and an organic solvent to elute the nucleic acid from the beads.

As used herein, the term "nonporous" is defined to denote a bead which has surface pores having a diameter that is less than the size and shape of the smallest DNA fragment in the separation in the solvent medium used therein. Included in this definition are polymer beads having these specified maximum size restrictions in their natural state or which have been treated to reduce their pore size to meet the maximum effective pore size required.

The surface conformations of nonporous beads of the present invention can include depressions and shallow pit-like structures which do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the polynucleotide into the interconnected pore structure and into the bead impair the resolution of separations or result in separations that have very long retention times. In MIPC, however, the beads are "nonporous" and the polynucleotides do not enter the bead structure.

Chromatographic efficiency of the column beads is predominantly influenced by the properties of surface and near-surface areas. For this reason, the following descriptions are related specifically to the close-to-the-surface region of the polymeric beads. The main body and/or the center of such beads can exhibit entirely different chemistries and sets of physical properties from those observed at or near the surface of the polymeric beads of the present invention.

The nonporous polymeric beads of the present invention are prepared by a two-step process. in which small seed beads are initially produced by emulsion polymerization of suitable polymerizable monomers. The emulsion polymerization procedure of the invention is a modification of the procedure of Goodwin, et al. (Colloid & Polymer Sci., 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term alkyl as used herein in reference to the beads of the present invention is defined to include alkyl and alkyl substituted aryl groups, having from 1 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

The chromatographic material reported in the Bonn patent was limited to nonporous beads substituted with alkyl groups having at least 3 carbons because Bonn et al. were unsuccessful in obtaining separations using polymer beads lacking this substitution. Additionally, the polymer beads were limited to a small group of vinyl aromatic monomers, and Bonn et al. were unable to effect double stranded DNA separations with other materials.

In the present invention, successful separation of double stranded DNA can be achieved using underivatized nonporous beads as well as using beads derivatized with alkyl groups having 1 to 1,000,000 carbons.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly (ethylvinylbenzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, must provide a nonporous, non-reactive, and non-polar surface for the MIPC separation.

In an important aspect of the present invention, the beads and other media of the invention are characterized by being substantially free from multivalent cations which are free to bind with DNA. The preferred beads of the present invention are characterized by having been subjected to precautions during production, including a decontamination treatment, such as an acid wash treatment, designed to substantially eliminate any multivalent cation contaminants (e.g. Fe(III), Cr(III), or colloidal metal contaminants). Only very pure, non-metal containing materials should be used in the production of the beads in order that the resulting beads will have minimum metal content.

In addition to the beads themselves being substantially metal-free, Applicants have also found that, to achieve optimum peak separation during MIPC, the separation column and all process solutions held within the column or flowing through the column are preferably substantially free of multivalent cation contaminants. As described in commonly owned U.S. Pat. Nos. 5,772,889; 5,997,742; and 5,972,222, and in co-pending U.S. patent applications Ser. No. 09/080,547, this can be achieved by supplying and feeding solutions that enter the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer.

There are two places where multivalent cation binding agents, e.g., chelators, are used in MIPC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent must not interfere with the chromatographic process.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, a-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation binding agent is EDTA.

To achieve high resolution chromatographic separations of polynucleotides, it is generally necessary to tightly pack the chromatographic column with the solid phase polymer beads. Any known method of packing the column with a column packing material can be used in the present invention to obtain adequate high resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a 50×7.8 mm ID column, 3.0 grams of beads can be suspended in 15 mL of methanol with the aid of sonication. The suspension is then packed into the column using 100 mL of methanol at 8,000 psi of pressure. This improves the density of the packed bed.

The separation method of the invention is generally applicable to the chromatographic separation of single stranded and double stranded polynucleotides of DNA and RNA. Samples containing mixtures of polynucleotides can result from total or enzymatic synthesis of polynucleotides, cleavage of DNA or RNA with endonucleases or with other enzymes or chemicals, as well as nucleic acid samples which have been multiplied and amplified using polymerase chain reaction techniques.

The improved method of the present invention can be used to separate double stranded polynucleotides having up to about 10,000 base pairs. The method can be used to separate polynucleotides having between about 5 to about 15,000–20,000 nucleotides.

In a preferred embodiment, the separation is by Matched Ion Polynucleotide Chromatography (MIPC). The nonporous beads of the invention are used as a reverse phase material that will function with counterion agents and a solvent gradient to effect the DNA separations. In MIPC, the polynucleotides are paired with a counterion and then subjected to reverse phase chromatography using the nonporous beads of the present invention.

There are several types of counterions suitable for use with MIPC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

The purpose of the alkyl group is to impart a nonpolar character to the polynucleic acid through a matched ion process so that the polynucleic acid can interact with the nonpolar surface of the separation media. The requirements for the extent of nonpolarity of the counterion-DNA pair depends on the polarity of the separation media, the solvent conditions required for separation, the particular size and type of fragment being separated. For example, if the polarity of the separation media is increased, then the polarity of the counterion agent may have to change to match the polarity of the surface and increase interaction of the counterion-DNA pair. Triethylammonium acetate is preferred although quaternary ammonium reagents such as tetrapropyl or tetrabutyl ammonium salts can be used when extra nonpolar character is needed or desired. In general, as the polarity of the alkyl group is increased, size specific separations, sequence independent separations become more possible. Quaternary counterion reagents are not volatile, making removal of the reagent more difficult.

In some cases, it may be desired to increase the range of concentration of organic solvent used to perform the separation. For example, increasing the alkyl length on the counterion agent will increase the nonpolarity of the counterion-DNA pair resulting in the need to either increase the concentration of the mobile phase organic solvent, or increase the strength of the organic solvent type, e.g. acetonitrile is about two times more effective than methanol for eluting polynucleic acids. There is a positive correlation between concentration of the organic solvent required to elute a fragment from the column and the length of the fragment. However, at high organic solvent concentrations, the polynucleotide could precipitate. To avoid precipitation, a strong organic solvent or a smaller counterion alkyl group can be used. The alkyl group on the counterion reagent can also be substituted with halides, nitro groups, or the like to moderate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkyalmmonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography*, 2nd Ed., Dr. Alfred H üthig Verlag Heidelberg (1987). Counterion agents that are volatile are preferred for use in the method of the invention, with triethylammonium acetate (TEAA) and triethylammonium hexafluoroisopropyl alcohol being most preferred.

Other features of the invention will become apparent in the course of the following descriptions of exemplary embodiments which are given for illustration of the invention and are not intended to be limiting thereof.

EXAMPLE 1

DNA Fragment Sizing by MIPC Using a 4.6 mm ID Column

MIPC analysis of pGEM DNA size markers (Part No. G174A, Promega Corp., Madison, Wis.) was performed using octadecyl modified, nonporous poly (ethylvinylbenzene-divinylbenzene) beads packed in a 50 mm×4.6 mm ID separation column (DNASEP® cartridge, Transgenomic, Inc., San Jose, Calif.) and using a WAVE® DNA Fragment Analysis System (Transgenomic). Eluent A: 0.1 M TEM, pH 7.0; eluent B: 0.1 TEM, 25% (v/v) acetonitrile, pH 7.0. The gradient conditions were as follows:

| Time (min) | % A | % B |
| --- | --- | --- |
| 0.0 | 64 | 36 |
| 0.5 | 56 | 44 |
| 12.8 | 35 | 65 |
| 25.0 | 31 | 69 |
| 37.3 | 28 | 72 |
| 49.5 | 25 | 75 |
| 49.6 | 0 | 100 |
| 51.6 | 0 | 100 |
| 51.7 | 64 | 36 |
| 53.7 | 64 | 36 |

The flow rate was 0.9 mL/min and the column temperature was 50° C. UV detection was performed at 260 nm. Injection volume was 10 µL. 80 µL of 0.1 M TEAA was mixed with 20 µL of pGEM® DNA Marker prior to injection. The amount of DNA injected was 2 µg. The chromatogram is shown in FIG. 15.

EXAMPLE 2

DNA Fragment Sizing by MIPC Using a 7.8 mm ID Column

Figure 16:
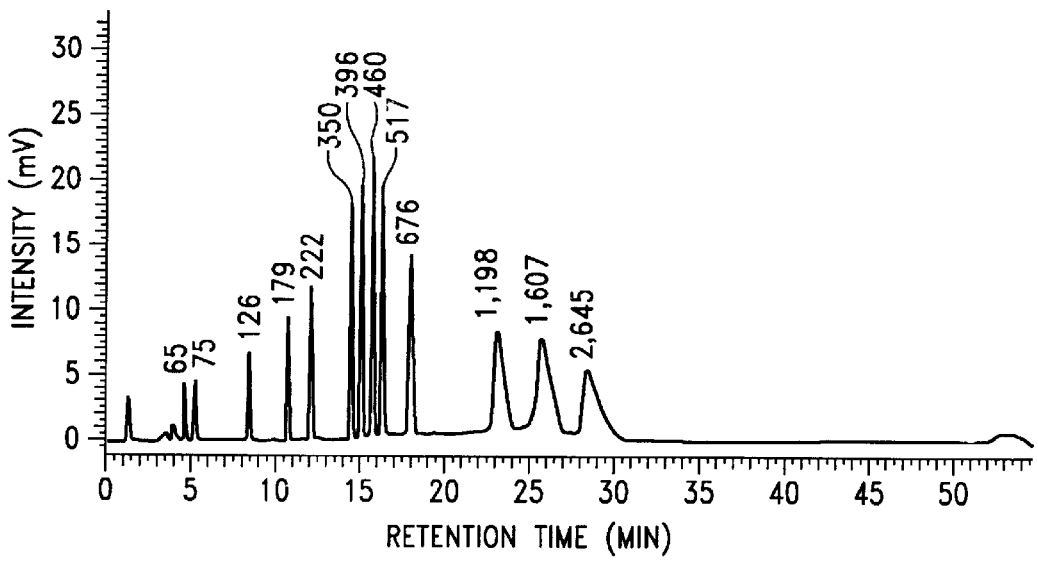
FIG. 16 is a MIPC separation of pGEM DNA markers on a 50 mm×7.8 mm ID column. Peaks are labeled with the number of base pairs of the eluted fragment.

Analysis of the pGEM DNA Markers was performed using the same conditions as described in Example 1 except that the separation column was replaced by a 50 mm×7.8 mm ID column packed with separation beads from the same lot. The chromatogram is shown in FIG. 16.

EXAMPLE 3

Separation of Homoduplex and Heteroduplex DNA by DMIPC Using a 4.6 mm ID Column

DMIPC analysis of a 209 bp mutation standard was performed using a DNASEP® 50 mm×4.6 mm ID separation column and using a WAVE® DNA Fragment Analysis System (Transgenomic). Eluent A: 0.1 M TEM, pH 7.0; eluent B: 0.1 TEM, 25% (v/v) acetonitrile, pH 7.0. The gradient conditions were as follows:

| Time (min) | % A | % B |
|---|---|---|
| 0 | 50 | 50 |
| 0.5 | 47 | 53 |
| 4.0 | 40 | 60 |
| 5.5 | 0 | 100 |
| 6.5 | 50 | 50 |
| 8.5 | 50 | 50 |

The flow rate was 0.9 mL/min at 50° C. UV detection was performed at 260 nm. The standard mixture was hybridized as recommended by the vendor (Trangenomic). Injection volume was 4 μL. The mutation separation profile is shown in FIG. 18.

The mutation standard (part no. 440582 from Transgenomic) contained a 209 base pair fragment from the human Y chromosome, locus DYS271 with an A to G mutation at position 168 as described by Seielstad et al., *Hum. Mol. Genet.* 3:2159 (1994).

EXAMPLE 4

Separation of Homoduplex and Heteroduplex DNA by DMIPC Using a 7.8 mm ID column

Figure 19:
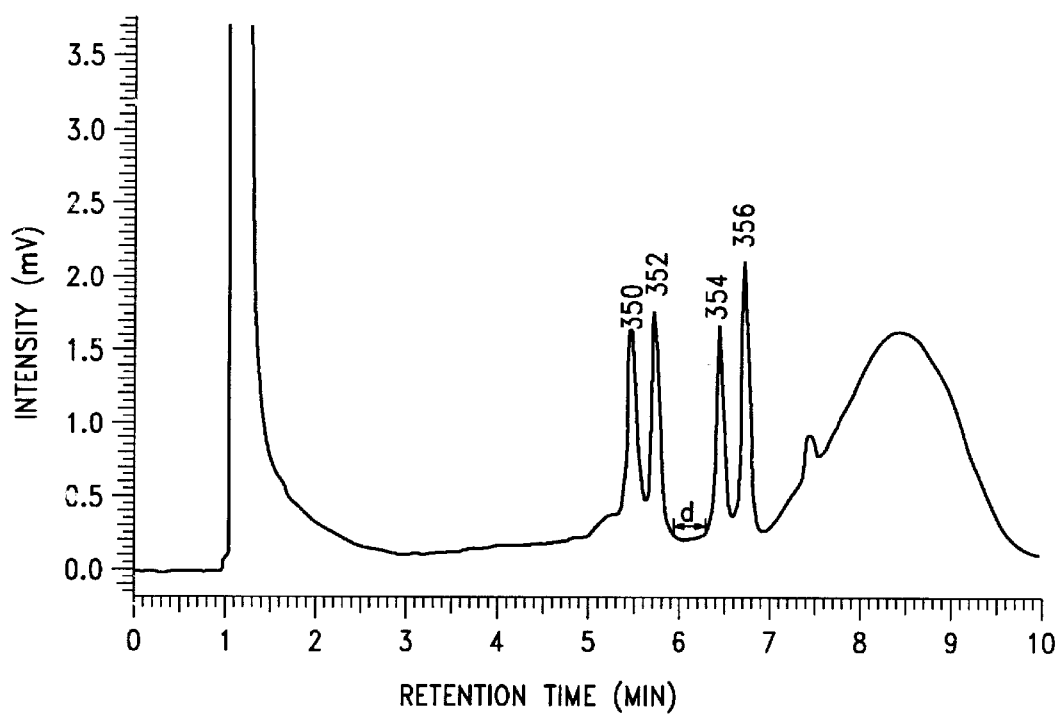
FIG. 19 is a mutation separation profile of a 209 bp homoduplex/heteroduplex mixture using a 50 mm×7.8 mm ID column.

Analysis of the 209 base pair mutation standard was performed using the same conditions as described in Example 3 except that the separation column was replaced by a 50 mm×7.8 mm ID column packed with separation beads from the same batch as those used Example 3. The chromatogram is shown in FIG. 19.

EXAMPLE 5

Preparation of Nonporous Poly(styrene-divinylbenzene) Particles

Sodium chloride (0.236 g) was added to 354 mL of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 mL of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 mL volume of suspension resulting from the first step. The amount of polymerized styrene in 1000 mL was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased.

The protocol for the second step is based on the activated swelling method described by Ugelstad et al. (Adv. *Colloid Interface Sci.*, 13:101–140 (1980)). In order to initiate activated swelling, or the second synthetic step, the aqueous suspension of polystyrene seeds (200 ml) from the first step was mixed first with 60 mL of acetone and then with 60 mL of a 1-chlorododecane emulsion. To prepare the emulsion, 0.206 g of sodium dodecylsulfate, 49.5 mL of deionized water, and 10.5 mL of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C.

Following the removal of acetone, the swollen beads were further grown by the addition of 310 g of a ethyldivinylbenzene and divinylbenzene (DVB) (1:1.71) mixture also containing 2.5 g of dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30 Å).

After drying, the dried beads (10 g) from step two were washed four times with 100 mL of n-heptane, and then two times with each of the following: 100 mL of diethylether, 100 mL of dioxane, and 100 mL of methanol. Finally, the beads were dried.

EXAMPLE 6

Alkylation of Poly(Styrene-Divinylbenzene) Polymer Beads

The following procedures were carried out under nitrogen (Air Products, Ultra Pure grade, Allentown, Pa.) at a flow rate of 250–300 mL/min. 25 g of the beads prepared in Example 5 were suspended in 150–160 g of 1-chlorooctadecane (product no. 0235, TCI America, Portland, Oreg.) using a bow shaped mixer (use a 250 mL wide neck Erlenmeyer flask). The temperature was set to 50–60° C. to prevent the 1-chlorooctadecane from solidifying. Larger pieces of polymer were broken up to facilitate suspending. The solution was mixed using a stirrer (Model RZRI, Caframo, ONT NOH2T0, Canada) with the speed set at 2. The polymer suspension was transferred into a three neck bottle (with reflux condenser, overhead stirrer and gas inlet). 52–62 g of 1-chlorooctadecane were used to rinse the Erlenmeyer flask and were added to the three neck bottle. The bottle was heated in an ethylene glycol bath set at 80° C. The solution was mixed using a stirrer (Caframo) with the speed set at 0. After 20 minutes, the reaction was started by addition of 1.1 g $AICl_3$ powder (product no. 06218, Fluka, Milwaukee, Wis.) and continued for 16–18 h.

After the reaction, the polymer was separated from excess 1-chlorooctadecane by centrifugation followed by consecutive washing steps:

| Addition | Comment |
|---|---|
| 50 mL conc. HCl, 50–60 mL n-heptane | 4 repetitions, with recycled heptane |
| 100 mL H₂O, 50–60 mL n-heptane | 1 repetition, with fresh heptane |
| 50 mL conc. HCl, 50–60 mL n-heptane | 1 repetition, with fresh heptane |
| 100 mL H₂O, 50–60 mL n-heptane | 1 repetition, fresh heptane |
| 150 mL H₂O, no n-heptane | 3 repetitions, use plastic stirrer to break up chuncks of polymer beads. Repeat steps 4 and 5 three times. Shake for two minutes with no centrifugation. |
| 100 mL THF | 3 repetitions |
| 100 mL THF/n-heptane | 1 repetition |
| 100 mL n-heptane | 1 repetition |
| 100 mL THF | 1 repetition |
| 100 mL CH₃OH | 4 repetitions |

In the steps where aqueous solvents (HCl or H$_2$O) were used, the polymer was shaken for 30 seconds with the aqueous phase before adding n-heptane. n-Heptane was then added and the mixture was shaken vigorously for 2 min. After the final polymeric beads were dried at 40–50° C. for 2–3 hr, they were ready for packing.

EXAMPLE 7

Acid Wash Treatment

The beads prepared in Example 6 were washed three times with tetrahydrofuran and two times with methanol. Finally the beads were stirred in a mixture containing 100 mL tetrahydrofuran and 100 mL concentrated hydrochloric acid for 12 hours. After this acid treatment, the polymer beads were washed with a tetrahydrofuran/water mixture until neutral (pH=7). The beads were then dried at 40° C. for 12 hours.

EXAMPLE 8

Column Packing Procedure

After weighing out 3 grams of oven dried polymeric beads, form a slurry with 10 mL tetrahydrofuran (THF) and place in a sonicator under a fume hood for 15 min. The add 5 mL of THF and 5 mL of methanol (MeOH) and sonicate an additional 10 min. Pre-fill a packing assembly with 20 mL MeOH. Pour the slurry slowly into the packing assembly. Turn on a Haskel pump (Haskel International, Inc., Burbank, Calif.) and slowly increase packing pressure to 5000 psi for the initial packing phase. After 10 min, slowly increase packing pressure to 9000 psi and set the secondary packing phase for 20 min. After 20 min, change the packing eluent from MeOH to 0.05 M Na$_4$EDTA. Then set the final packing phase for 40 min.

EXAMPLE 9

DNA Fragment Sizing by MIPC Using a 4.6 mm ID Column

MIPC analysis of λ DNA Hind III digest (containing fragments of sizes 125; 564, 2027, 2322, 4361, 6557, 9416 and 23130 bp) (part no. 030204, Kramel Biotech, Transgenomic Ltd., Northumberland, UK) was performed using octadecyl modified, nonporous poly(ethylvinylbenzene-divinylbenzene) beads packed in a 50 mm×4.6 mm ID separation column (DNASEP® cartridge) and using a WAVE® DNA Fragment Analysis System. Eluent A: 0.1 M TEAA, pH 7.0; eluent B: 0.1 TEAA, 25% (v/v) acetonitrile, pH 7.0. The gradient conditions were as follows:

| Time (min) | % A | % B | Flow (mL/min) |
|---|---|---|---|
| 0.0 | 65 | 35 | 0.9 |
| 1.0 | 60 | 40 | 0.9 |
| 17.0 | 28 | 72 | 0.9 |
| 17.1 | 0 | 100 | 0.9 |
| 18.1 | 0 | 100 | 0.9 |
| 18.2 | 65 | 35 | 0.9 |
| 20.1 | 65 | 35 | 0.9 |

Figure 20:
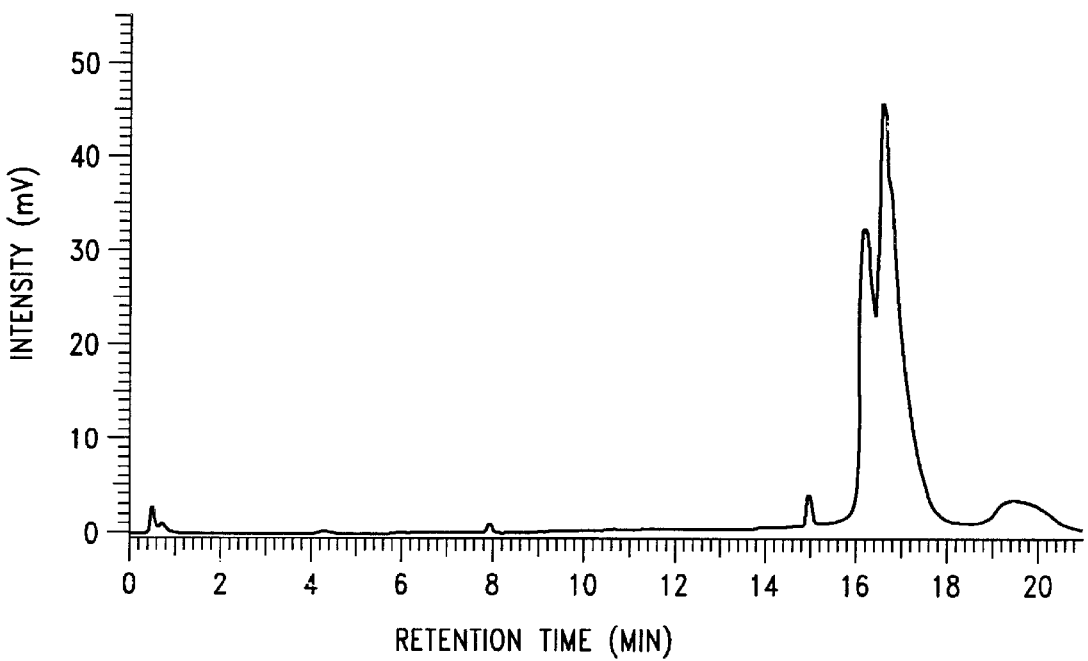
FIG. 20 is a MIPC separation of a λ DNA Hind III digest standard on a 50 mm×4.6 mm ID column.

The mobile phase solutions were prepared from concentrated triethylammonium acetate (100 mL Transgenomic part No. 553301) to give A=0.1 M TEAA, pH 7, B=0.1M TEAA and 25% acetonitrile. The flow rate was 0.9 mL/min and the column temperature was 50° C. UV detection was performed at 260 nm. 40 μL of 0.1 M TEAA was mixed with 100 μL of λ DNA Hind III digest solution. Injection volume was 15 μL. The amount of DNA injected was 2 μg. The chromatogram is shown in FIG. 20.

EXAMPLE 10

DNA Fragment Sizing by MIPC Using a 7.8 mm ID Column

Figure 21:
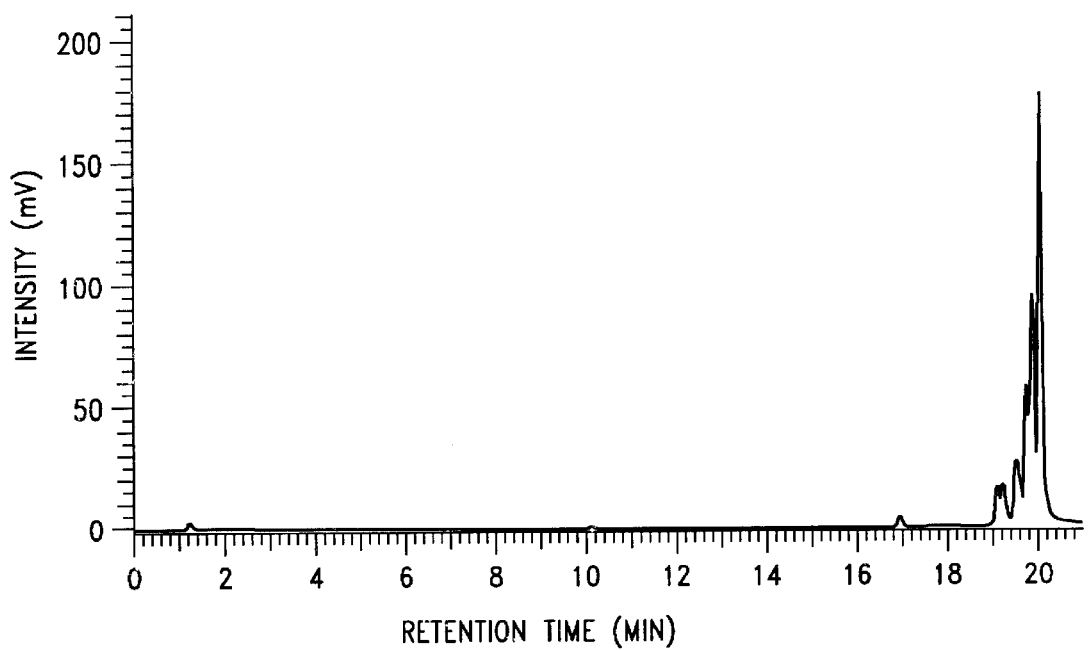
FIG. 21 is a MIPC separation of a λ DNA Hind III digest standard on a 50 mm×7.8 mm ID column.

Analysis of the λ DNA Hind III digest was performed using the same conditions as described in Example 9 except that the separation column was replaced by a 50 mm×7.8 mm ID packed column. The chromatogram is shown in FIG. 21.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. An improved method for separating a mixture of double stranded DNA fragments by Matched Ion Polynucleotide Chromatography, the mixture comprising fragments having lengths exceeding about 1000 base pairs, the method comprising:
  a) applying a solution of said fragments and counterion reagent to separation beads, said beads retained within a separation column, said beads having an average diameter of 1 to 100 microns, said beads being unsubstituted polymer beads or polymer beads substituted with a hydrocarbon moiety having from 1 to 1,000,000 carbons, wherein said beads are characterized by being substantially free from multivalent cations which are free to bind with DNA, said column having an ID greater than about 5 mm;
  b) eluting said fragments with a gradient eluting solvent of increasing organic component concentration containing a counterion agent;
     wherein surfaces which are contacted by the solution of the fragments and the eluting solvent are materials which do not trap or release multivalent metal cations therefrom;
     wherein said eluting is carried out under conditions effective to at least partially denature said heteroduplexes and where said eluting results in the separation of said heteroduplexes from said homoduplexes.

2. A method of claim 1 wherein said ID is greater than about 7 mm.

3. A method of claim 1 wherein said ID is greater than about 10 mm.

4. A method of claim 1 wherein said ID is greater than about 50 mm.

5. A method of claim 1 wherein said ID is in the range of about 5 mm to about 1 m.

6. An improved method for separating heteroduplex and homoduplex DNA molecules in a mixture, comprising:

a) applying a solution of said fragments and counterion reagent to separation beads, said beads retained within a separation column, said beads having an average diameter of 1 to 100 microns, said beads being unsubstituted polymer beads or polymer beads substituted with a hydrocarbon moiety having from 1 to 1,000,000 carbons, wherein said beads are characterized by being substantially free from multivalent cations which are free to bind with DNA, said column having an ID greater than about 5 mm;

b) eluting said fragments with a gradient eluting solvent of increasing organic component concentration containing a counterion agent;

wherein surfaces which are contacted by the solution of the fragments and the eluting solvent are materials which do not trap or release multivalent metal cations therefrom;

wherein said eluting is carried out under conditions effective to at least partially denature said heteroduplexes and where said eluting results in the separation of said heteroduplexes from said homoduplexes.

7. An method of claim 6 wherein said ID is greater than about 7 mm.

8. An method of claim 6 wherein said ID is greater than about 10 mm.

9. An method of claim 6 wherein said ID is greater than about 50 mm.

10. An method of claim 6 wherein said ID is in the range of about 5 mm to about 1 m.

* * * * *